US010653446B2

(12) United States Patent
Andreas et al.

(10) Patent No.: US 10,653,446 B2
(45) Date of Patent: *May 19, 2020

(54) TYMPANOSTOMY TUBE DELIVERY DEVICE WITH CUTTING DILATOR

(71) Applicant: Tusker Medical, Inc., Menlo Park, CA (US)

(72) Inventors: Bernard H. Andreas, Redwood City, CA (US); T. Daniel Gross, Los Gatos, CA (US); Mathew D. Clopp, Santa Clara, CA (US); Arkady Kokish, Los Gatos, CA (US)

(73) Assignee: TUSKER MEDICAL, INC., Menlo Park, CA (US)

( * ) Notice: Subject to any disclaimer, the term of this patent is extended or adjusted under 35 U.S.C. 154(b) by 212 days.

This patent is subject to a terminal disclaimer.

(21) Appl. No.: 15/626,756

(22) Filed: Jun. 19, 2017

(65) Prior Publication Data

US 2017/0281230 A1 Oct. 5, 2017

Related U.S. Application Data

(63) Continuation of application No. 13/804,612, filed on Mar. 14, 2013, now Pat. No. 9,681,891.

(51) Int. Cl.
*A61B 17/34* (2006.01)
*A61F 11/00* (2006.01)
*A61B 17/00* (2006.01)

(52) U.S. Cl.
CPC ........ *A61B 17/3468* (2013.01); *A61F 11/002* (2013.01); *A61B 2017/00477* (2013.01)

(58) Field of Classification Search
CPC ............ A61B 17/3417; A61B 17/3468; A61B 2017/346; A61B 2017/3454; A61F 11/002
See application file for complete search history.

(56) References Cited

U.S. PATENT DOCUMENTS

| 858,673 A | 7/1907 | Roswell |
| 1,920,006 A | 7/1933 | Dozier et al. |

(Continued)

FOREIGN PATENT DOCUMENTS

| CN | 86105171 A | 3/1987 |
| CN | 2635015 Y | 8/2004 |

(Continued)

OTHER PUBLICATIONS

Office Action for U.S. Appl. No. 10/841,420, dated Aug. 5, 2008, 11 pages.

(Continued)

*Primary Examiner* — Sarah W Aleman

(57) ABSTRACT

A tympanostomy tube delivery device comprises a body, a cannula extending distally from the body, and a cylindraceous member disposed within the cannula. The cylindraceous member comprises a tubular portion and a plurality of leaves positioned at the distal end of the tubular portion. The leaves are movable between a collapsed position and an expanded position. The cylindraceous member is slidable relative to the cannula to selectively expose the leaves relative to the open distal end of the cannula. A first leaf of the plurality of leaves has a sharp distal point configured to pierce a tympanic membrane and a longitudinally extending sharp edge. The cylindraceous member may be used to create and dilate a myringotomy incision in a tympanic membrane. The tympanostomy tube delivery device may then be used to deploy a tympanostomy tube through the myringotomy incision.

18 Claims, 21 Drawing Sheets

(56) References Cited

U.S. PATENT DOCUMENTS

| | | |
|---|---|---|
| 2,162,681 A | 6/1939 | Ryan |
| 3,473,170 A | 10/1969 | Haase et al. |
| 3,638,643 A | 2/1972 | Hotchkiss |
| 3,741,197 A | 6/1973 | Sanz et al. |
| 3,807,404 A | 4/1974 | Weissman et al. |
| 3,888,258 A | 6/1975 | Akiyama |
| 3,897,786 A | 8/1975 | Garnett et al. |
| 3,913,584 A | 10/1975 | Walchle et al. |
| 3,948,271 A | 4/1976 | Akiyama |
| 3,991,755 A | 11/1976 | Vernon et al. |
| 4,168,697 A | 9/1979 | Cantekin |
| 4,335,713 A | 6/1982 | Komiya |
| 4,335,715 A | 6/1982 | Kirkley |
| 4,380,998 A | 4/1983 | Kieffer, III et al. |
| 4,406,282 A | 9/1983 | Parker et al. |
| 4,468,218 A | 8/1984 | Armstrong |
| 4,473,073 A | 9/1984 | Darnell |
| 4,552,137 A | 11/1985 | Strauss |
| 4,564,009 A | 1/1986 | Brinkhoff |
| 4,712,537 A | 12/1987 | Pender |
| 4,750,491 A | 6/1988 | Kaufman et al. |
| 4,796,624 A | 1/1989 | Trott et al. |
| 4,800,876 A | 1/1989 | Fox et al. |
| 4,913,132 A | 4/1990 | Gabriel |
| 4,946,440 A | 8/1990 | Hall |
| 4,964,850 A | 10/1990 | Bouton et al. |
| 4,968,296 A | 11/1990 | Ritch et al. |
| 4,971,076 A | 11/1990 | Densert et al. |
| 5,026,378 A | 6/1991 | Goldsmith, III |
| 5,044,373 A | 9/1991 | Northeved et al. |
| 5,047,007 A | 9/1991 | McNichols et al. |
| 5,053,040 A | 10/1991 | Goldsmith, III |
| 5,092,837 A | 3/1992 | Ritch et al. |
| 5,107,861 A | 4/1992 | Narboni |
| 5,135,478 A | 8/1992 | Sibalis |
| 5,158,540 A | 10/1992 | Wijay |
| 5,178,623 A | 1/1993 | Cinberg et al. |
| 5,254,120 A | 10/1993 | Cinberg et al. |
| 5,261,903 A | 11/1993 | Dhaliwal et al. |
| D352,780 S | 11/1994 | Glaeser et al. |
| 5,370,656 A | 12/1994 | Shevel |
| 5,421,818 A | 6/1995 | Arenberg |
| 5,466,239 A | 11/1995 | Cinberg et al. |
| 5,489,286 A | 2/1996 | Cinberg et al. |
| 5,496,329 A | 3/1996 | Reisinger |
| D378,611 S | 3/1997 | Croley |
| 5,610,988 A | 3/1997 | Miyahara |
| 5,643,280 A | 7/1997 | Del Rio et al. |
| 5,645,584 A | 7/1997 | Suyama |
| 5,658,235 A | 8/1997 | Priest et al. |
| 5,674,196 A | 10/1997 | Donaldson et al. |
| 5,676,635 A | 10/1997 | Levin |
| 5,681,323 A | 10/1997 | Arick |
| D387,863 S | 12/1997 | Herman et al. |
| 5,707,383 A | 1/1998 | Bays et al. |
| 5,775,336 A | 7/1998 | Morris |
| 5,782,744 A | 7/1998 | Money |
| 5,792,100 A | 8/1998 | Shantha |
| 5,810,848 A | 9/1998 | Hayhurst |
| 5,827,295 A | 10/1998 | Del Rio et al. |
| 5,893,828 A | 4/1999 | Uram |
| 5,893,837 A | 4/1999 | Eagles et al. |
| 5,984,930 A | 11/1999 | Maciunas et al. |
| D418,223 S | 12/1999 | Phipps et al. |
| D420,741 S | 2/2000 | Croley |
| 6,022,342 A | 2/2000 | Mukherjee |
| 6,024,726 A | 2/2000 | Hill |
| 6,039,748 A | 3/2000 | Savage et al. |
| 6,045,528 A | 4/2000 | Arenberg et al. |
| D424,197 S | 5/2000 | Sydlowski et al. |
| 6,059,803 A | 5/2000 | Spilman |
| D426,135 S | 6/2000 | Lee |
| 6,077,179 A | 6/2000 | Liechty, II |
| 6,110,196 A | 8/2000 | Edwards |
| 6,137,889 A | 10/2000 | Shennib et al. |
| 6,171,236 B1 | 1/2001 | Bonutti |
| 6,183,469 B1 | 2/2001 | Thapliyal et al. |
| 6,200,280 B1 | 3/2001 | Brenneman et al. |
| 6,206,888 B1 | 3/2001 | Bicek et al. |
| 6,245,077 B1 | 6/2001 | East et al. |
| 6,248,112 B1 | 6/2001 | Gambale et al. |
| 6,251,121 B1 | 6/2001 | Saadat |
| 6,258,067 B1 | 7/2001 | Hill |
| D450,843 S | 11/2001 | McGuckin, Jr. et al. |
| 6,319,199 B1 | 11/2001 | Sheehan et al. |
| 6,358,231 B1 | 3/2002 | Schindler et al. |
| 6,398,758 B1 | 6/2002 | Jacobsen et al. |
| 6,416,512 B1 | 7/2002 | Ellman et al. |
| 6,440,102 B1 | 8/2002 | Arenberg et al. |
| 6,447,522 B2 | 9/2002 | Gambale et al. |
| 6,475,138 B1 | 11/2002 | Schechter et al. |
| 6,512,950 B2 | 1/2003 | Li et al. |
| 6,514,261 B1 | 2/2003 | Randall et al. |
| 6,520,939 B2 | 2/2003 | Lafontaine |
| 6,522,827 B1 | 2/2003 | Loeb et al. |
| 6,553,253 B1 | 4/2003 | Chang |
| 6,645,173 B1 | 11/2003 | Liebowitz |
| 6,648,873 B2 | 11/2003 | Arenberg et al. |
| 6,663,575 B2 | 12/2003 | Leysieffer |
| 6,682,558 B2 | 1/2004 | Tu et al. |
| 6,770,080 B2 | 8/2004 | Kaplan et al. |
| 6,916,159 B2 | 7/2005 | Rush et al. |
| 6,962,595 B1 | 11/2005 | Chamness et al. |
| 7,127,285 B2 | 10/2006 | Henley et al. |
| 7,137,975 B2 | 11/2006 | Miller et al. |
| D535,027 S | 1/2007 | James et al. |
| 7,160,274 B2 | 1/2007 | Ciok et al. |
| 7,344,507 B2 | 3/2008 | Briggs et al. |
| 7,351,246 B2 | 4/2008 | Epley |
| 7,381,210 B2 | 6/2008 | Zarbatany et al. |
| D595,410 S | 6/2009 | Luzon |
| 7,563,232 B2 | 7/2009 | Freeman et al. |
| D598,543 S | 8/2009 | Vogel et al. |
| 7,654,997 B2 | 2/2010 | Makower et al. |
| 7,677,734 B2 | 3/2010 | Wallace |
| 7,704,259 B2 | 4/2010 | Kaplan et al. |
| 7,749,254 B2 | 7/2010 | Sobelman et al. |
| D622,842 S | 8/2010 | Benoist |
| 7,909,220 B2 | 3/2011 | Viola |
| D640,374 S | 6/2011 | Liu et al. |
| 8,052,693 B2 | 11/2011 | Shahoian |
| 8,192,420 B2 | 6/2012 | Morriss et al. |
| 8,249,700 B2 | 8/2012 | Clifford et al. |
| 8,282,648 B2 | 10/2012 | Tekulve |
| 8,409,175 B2 | 4/2013 | Lee et al. |
| 8,425,488 B2 | 4/2013 | Clifford et al. |
| 8,498,425 B2 | 7/2013 | Graylin |
| 8,518,098 B2 | 8/2013 | Roeder et al. |
| 8,702,722 B2 | 4/2014 | Shahoian |
| 8,840,602 B2 | 9/2014 | Morriss et al. |
| 8,849,394 B2 | 9/2014 | Clifford et al. |
| 8,864,774 B2 | 10/2014 | Liu et al. |
| 8,998,927 B2 | 4/2015 | Kaplan et al. |
| 9,011,363 B2 | 4/2015 | Clopp et al. |
| 9,023,059 B2 | 5/2015 | Loushin et al. |
| 9,216,112 B2 | 12/2015 | Clifford et al. |
| 9,320,652 B2 | 4/2016 | Andreas et al. |
| 9,387,124 B2 | 7/2016 | Clifford |
| 9,539,146 B2 | 1/2017 | Girotra et al. |
| 9,681,891 B2 | 6/2017 | Andreas et al. |
| 9,707,131 B2 | 7/2017 | Shahoian |
| 9,770,366 B2 | 9/2017 | Liu et al. |
| 9,833,359 B2 | 12/2017 | Clopp |
| 9,833,360 B2 | 12/2017 | Andreas et al. |
| 9,833,601 B2 | 12/2017 | Clifford |
| 10,130,515 B2 | 11/2018 | Kaplan et al. |
| 10,195,086 B2 | 2/2019 | Van et al. |
| 10,219,950 B2 | 3/2019 | Andreas et al. |
| 10,258,776 B2 | 4/2019 | Clifford et al. |
| 2001/0020173 A1 | 9/2001 | Klumb et al. |
| 2002/0026125 A1 | 2/2002 | Leysieffer |
| 2002/0069883 A1 | 6/2002 | Hirchenbain |
| 2002/0111585 A1 | 8/2002 | Lafontaine |
| 2002/0138091 A1 | 9/2002 | Pflueger |

(56) References Cited

U.S. PATENT DOCUMENTS

| | | |
|---|---|---|
| 2002/0161379 A1 | 10/2002 | Kaplan et al. |
| 2002/0169456 A1 | 11/2002 | Tu et al. |
| 2003/0018291 A1 | 1/2003 | Hill et al. |
| 2003/0040717 A1 | 2/2003 | Saulenas et al. |
| 2003/0060799 A1 | 3/2003 | Arenberg et al. |
| 2003/0097178 A1 | 5/2003 | Roberson et al. |
| 2003/0120292 A1 | 6/2003 | Park et al. |
| 2003/0187456 A1 | 10/2003 | Perry |
| 2003/0199791 A1 | 10/2003 | Boecker et al. |
| 2004/0054339 A1 | 3/2004 | Ciok et al. |
| 2004/0064024 A1 | 4/2004 | Sommer |
| 2005/0033343 A1 | 2/2005 | Chermoni |
| 2005/0070765 A1 | 3/2005 | Abdelgany et al. |
| 2005/0165368 A1 | 7/2005 | Py et al. |
| 2005/0182385 A1 | 8/2005 | Epley |
| 2005/0187546 A1 | 8/2005 | Bek et al. |
| 2005/0203552 A1 | 9/2005 | Laufer et al. |
| 2005/0235422 A1 | 10/2005 | Wallace |
| 2005/0240147 A1 | 10/2005 | Makower et al. |
| 2006/0004323 A1 | 1/2006 | Chang et al. |
| 2006/0095050 A1 | 5/2006 | Hartley et al. |
| 2006/0142700 A1 | 6/2006 | Sobelman et al. |
| 2006/0155304 A1 | 7/2006 | Kaplan et al. |
| 2006/0161218 A1 | 7/2006 | Danilov |
| 2006/0163313 A1 | 7/2006 | Larson |
| 2006/0282062 A1 | 12/2006 | Ishikawa et al. |
| 2007/0088247 A1 | 4/2007 | Bliweis et al. |
| 2007/0233222 A1 | 10/2007 | Roeder et al. |
| 2007/0276466 A1 | 11/2007 | Lavelle et al. |
| 2008/0027423 A1 | 1/2008 | Choi et al. |
| 2008/0051804 A1 | 2/2008 | Cottler et al. |
| 2008/0065011 A1 | 3/2008 | Marchand et al. |
| 2008/0083813 A1 | 4/2008 | Zemlock et al. |
| 2008/0212416 A1 | 9/2008 | Polonio et al. |
| 2008/0262468 A1 | 10/2008 | Clifford et al. |
| 2008/0262508 A1 | 10/2008 | Clifford et al. |
| 2008/0262510 A1 | 10/2008 | Clifford |
| 2009/0163828 A1 | 6/2009 | Turner et al. |
| 2009/0171271 A1 | 7/2009 | Webster et al. |
| 2009/0209972 A1 | 8/2009 | Loushin et al. |
| 2009/0299344 A1 | 12/2009 | Lee et al. |
| 2009/0299379 A1 | 12/2009 | Katz et al. |
| 2009/0299433 A1 | 12/2009 | Lee |
| 2010/0041447 A1 | 2/2010 | Graylin |
| 2010/0048978 A1 | 2/2010 | Sing et al. |
| 2010/0061581 A1 | 3/2010 | Soetejo et al. |
| 2010/0160819 A1 | 6/2010 | Parihar et al. |
| 2010/0198135 A1 | 8/2010 | Morriss et al. |
| 2010/0217296 A1 | 8/2010 | Morriss et al. |
| 2010/0274188 A1 | 10/2010 | Chang et al. |
| 2010/0324488 A1 | 12/2010 | Smith |
| 2011/0015645 A1 | 1/2011 | Liu et al. |
| 2011/0022069 A1 | 1/2011 | Mitusina |
| 2011/0077579 A1 | 3/2011 | Harrison et al. |
| 2011/0288559 A1 | 11/2011 | Shahoian |
| 2012/0074200 A1 | 3/2012 | Schmid et al. |
| 2012/0130252 A1 | 5/2012 | Pohjanen et al. |
| 2012/0179187 A1 | 7/2012 | Loushin et al. |
| 2012/0265097 A1* | 10/2012 | Melchiorri ......... A61B 10/0266 600/567 |
| 2012/0283563 A1 | 11/2012 | Moore et al. |
| 2012/0310145 A1 | 12/2012 | Clifford et al. |
| 2013/0030456 A1 | 1/2013 | Assell et al. |
| 2013/0090544 A1 | 4/2013 | Clifford et al. |
| 2013/0338678 A1 | 12/2013 | Loushin et al. |
| 2014/0094733 A1 | 4/2014 | Clopp et al. |
| 2014/0100584 A1 | 4/2014 | Konstorum et al. |
| 2014/0194891 A1 | 7/2014 | Shahoian |
| 2014/0276906 A1 | 9/2014 | Andreas et al. |
| 2014/0277050 A1 | 9/2014 | Andreas et al. |
| 2015/0142029 A1 | 5/2015 | Fahn et al. |
| 2015/0164695 A1 | 6/2015 | Liu |
| 2015/0209509 A1 | 7/2015 | O'Cearbhaill et al. |
| 2015/0305944 A1 | 10/2015 | Kaplan et al. |
| 2015/0320550 A1 | 11/2015 | Downing et al. |
| 2016/0038341 A1 | 2/2016 | Clopp et al. |
| 2016/0038342 A1 | 2/2016 | Van et al. |
| 2016/0045369 A1 | 2/2016 | Clopp |
| 2016/0045370 A1 | 2/2016 | Andreas et al. |
| 2016/0045371 A1 | 2/2016 | Girotra et al. |
| 2016/0213519 A1 | 7/2016 | Andreas et al. |
| 2017/0209310 A1 | 7/2017 | Girotra et al. |
| 2018/0055693 A1 | 3/2018 | Liu et al. |
| 2018/0085258 A1 | 3/2018 | Andreas et al. |
| 2018/0085563 A1 | 3/2018 | Clifford et al. |
| 2018/0116876 A1 | 5/2018 | Clopp |
| 2018/0303673 A1 | 10/2018 | Clopp et al. |
| 2018/0304059 A1 | 10/2018 | Clifford et al. |
| 2019/0083318 A1 | 3/2019 | Kaplan et al. |
| 2019/0201242 A1 | 7/2019 | Andreas et al. |
| 2019/0314205 A1 | 10/2019 | Van et al. |

FOREIGN PATENT DOCUMENTS

| | | | |
|---|---|---|---|
| CN | 1933761 A | 3/2007 | |
| CN | 102122067 A | 7/2011 | |
| CN | 102510746 A | 6/2012 | |
| CN | 102920491 A | 2/2013 | |
| CN | 103327881 A | 9/2013 | |
| CN | 107072690 A | 8/2017 | |
| DE | 19618585 | 11/1997 | |
| DE | 19918288 A1 | 10/2000 | |
| EP | 0214527 A1 | 3/1987 | |
| FR | 2526656 | 11/1983 | |
| JP | H 07-116190 A | 5/1995 | |
| JP | 2012-533359 A | 12/2012 | |
| JP | 2013-543396 A | 12/2013 | |
| TW | 201200098 A | 1/2012 | |
| WO | WO 1999/011175 A1 | 3/1999 | |
| WO | WO 1999/017825 | 4/1999 | |
| WO | WO 2001/028407 | 4/2001 | |
| WO | WO 2002/056756 | 7/2002 | |
| WO | WO 2006/119512 | 11/2006 | |
| WO | WO 2008/030485 | 3/2008 | |
| WO | WO 2008/036368 | 3/2008 | |
| WO | WO 2008/131195 | 10/2008 | |
| WO | WO 2009/010788 | 1/2009 | |
| WO | WO 2009/105619 | 8/2009 | |
| WO | WO 2011/008948 | * 1/2011 | ............ A61F 11/00 |
| WO | WO 2012/040430 | 3/2012 | |
| WO | WO 2012/040600 | 3/2012 | |
| WO | WO 2012/054934 | 4/2012 | |
| WO | WO 2014/075949 | 5/2014 | |
| WO | WO 2014/143543 | 9/2014 | |
| WO | WO 2014/158571 | 10/2014 | |
| WO | WO 2016/022899 | 2/2016 | |
| WO | WO 2016/025308 | 2/2016 | |
| WO | WO 2016/025309 | 2/2016 | |
| WO | WO 2016/025310 | 2/2016 | |
| WO | WO 2016/025453 | 2/2016 | |

OTHER PUBLICATIONS

Office Action for U.S. Appl. No. 10/841,420, dated Feb. 20, 2008, 11 pages.

Office Action for U.S. Appl. No. 10/841,420, dated Nov. 17, 2006, 9 pages.

Office Action for U.S. Appl. No. 10/841,420, dated Jul. 20, 2009, 14 pages.

Office Action for U.S. Appl. No. 10/841,420, dated May 12, 2009, 13 pages.

Office Action for U.S. Appl. No. 10/841,420, dated Aug. 22, 2007, 10 pages.

Office Action for U.S. Appl. No. 12/754,304, dated Sep. 26, 2013, 13 pages.

Office Action for U.S. Appl. No. 12/754,304, dated Sep. 14, 2012, 15 pages.

Office Action for U.S. Appl. No. 12/754,304, dated Nov. 9, 2010, 14 pages.

Office Action for U.S. Appl. No. 12/754,304, dated Apr. 29, 2014, 10 pages.

(56) References Cited

OTHER PUBLICATIONS

Office Action for U.S. Appl. No. 12/754,304, dated Mar. 1, 2013, 13 pages.
Office Action for U.S. Appl. No. 12/754,304, dated Apr. 28, 2011, 15 pages.
U.S. Appl. No. 60/912,902, filed Apr. 19, 207.
Patent Examination Report No. 1 for Australian Patent Application No. 2008242735, dated Aug. 8, 2012, 3 pages.
Patent Examination Report No. 1 for Australian Patent Application No. 2013209354, dated Oct. 13, 2014, 5 pages.
First Office Action for Chinese Patent Application No. 200880020861.9, dated Jul. 12, 2011, 10 pages.
Second Office Action for Chinese Patent Application No. 200880020861.9, dated Dec. 31, 2011, 3 pages.
Search Report for Chinese Patent Application No. 201310047126.X, dated Mar. 6, 2015, 2 pages.
Second Office Action for Chinese Patent Application No. 201310047126.X, dated Mar. 16, 2015, 10 pages.
Office Action for European Application No. 08746237.0, dated Mar. 24, 2016, 3 pages.
Office Action for European Application No. 08746237.0, dated Aug. 4, 2015, 7 pages.
Supplementary Partial Search Report for European Application No. 08746237.0, dated Jun. 30, 2014, 9 pages.
Notification of Reasons for Refusal for Japanese Patent Application No. 2010-504267, dated Nov. 20, 2012, 4 pages.
Notification of Reasons for Refusal for Japanese Patent Application No. 2010-504267, dated Nov. 12, 2013, 4 pages.
Office Action for U.S. Appl. No. 11/749,725, dated Dec. 4, 2014, 14 pages.
Office Action for U.S. Appl. No. 11/749,725, dated Dec. 28, 2010, 15 pages.
Office Action for U.S. Appl. No. 11/749,725, dated May 27, 2011, 14 pages.
International Search Report for International Application No. PCT/US2008/060779, dated Sep. 3, 2008.
Written Opinion for International Application No. PCT/US2008/060779, dated Sep. 3, 2008.
International Preliminary Report on Patentability for International Application No. PCT/US2008/060779, dated Nov. 17, 2009.
Office Action for U.S. Appl. No. 11/749,726, dated Mar. 16, 2010, 7 pages.
Office Action for U.S. Appl. No. 11/749,726, dated Jul. 21, 2010, 8 pages.
U.S. Appl. No. 11/749,729, filed May 16, 2007.
Office Action for U.S. Appl. No. 11/749,729, dated May 26, 2011, 11 pages.
Office Action for U.S. Appl. No. 11/749,729, dated Jun. 17, 2010, 8 pages.
Office Action for U.S. Appl. No. 11/749,729, dated Nov. 4, 2011, 12 pages.
Office Action for U.S. Appl. No. 11/749,729, dated Nov. 23, 2010, 9 pages.
U.S. Appl. No. 11/749,733, filed May 16, 2007.
Office Action for U.S. Appl. No. 11/749,733, dated Jun. 10, 2009, 13 pages.
Office Action for U.S. Appl. No. 11/749,733, dated Dec. 2, 2008, 9 pages.
Office Action for U.S. Appl. No. 11/749,733, dated Aug. 15, 2011, 17 pages.
Office Action for U.S. Appl. No. 11/749,733, dated Dec. 17, 2009, 18 pages.
Office Action for U.S. Appl. No. 11/749,733, dated Apr. 6, 2009, 13 pages.
Office Action for U.S. Appl. No. 11/749,734, dated Nov. 19, 2009, 13 pages.
Office Action for U.S. Appl. No. 11/749,734, dated Feb. 26, 2009, 14 pages.
Office Action for U.S. Appl. No. 11/749,734, dated Apr. 30, 2010, 14 pages.
Office Action for U.S. Appl. No. 11/749,734, dated Jul. 22, 2009, 12 pages.
Office Action for U.S. Appl. No. 13/164,993, dated May 28, 2013, 10 pages.
Office Action for U.S. Appl. No. 13/164,993, dated Aug. 28, 2012, 15 pages.
Office Action for U.S. Appl. No. 13/164,993, dated Jan. 16, 2013, 14 pages.
Office Action for U.S. Appl. No. 13/587,806, dated Feb. 13, 2013, 8 pages.
Office Action for U.S. Appl. No. 13/647,562, dated Jan. 5, 2015, 15 pages.
Office Action for U.S. Appl. No. 13/647,562, dated Dec. 13, 2013, 8 pages.
Office Action for U.S. Appl. No. 13/647,562, dated Jul. 30, 2015, 16 pages.
Office Action for U.S. Appl. No. 13/647,562, dated Jul. 2, 2014, 13 pages.
Office Action for U.S. Appl. No. 13/647,562, dated Dec. 1, 2016, 14 pages.
U.S. Appl. No. 11/962,063, filed Dec. 20, 2007.
U.S. Appl. No. 61/085,360, filed Jul. 31, 2008.
International Search Report for International Application No. PCT/US2009/052395, dated Nov. 6, 2009.
Written Opinion for International Application No. PCT/US2009/052395, dated Nov. 6, 2009.
International Search Repor and Written Opinion t for International Application No. PCT/US2010/058718, dated Feb. 17, 2011.
Written Opinion for International Application No. PCT/US2010/058718, dated Feb. 17, 2011.
U.S. Appl. No. 61/225,893, filed Jul. 15, 2009.
Patent Examination Report No. 1 for Australian Application No. 2010273372, dated Nov. 12, 2014, 2 pages.
Office Action for Canadian Application No. 2,768,009, dated Aug. 4, 2016, 4 pages.
First Office Action for Chinese Application No. 201080041755.6, dated Jul. 3, 2013.
Notification of Reasons for Refusal for Japanese Application No. 2012-520778, dated Feb. 18, 2014.
Office Action for Korean Application No. 10-2012-7003590, dated Sep. 27, 2016, 9 pages.
Communication of the Substantive Examination Report for Mexican Application No. MX/a/2012/000691, dated Apr. 24, 2014.
Office Action for U.S. Appl. No. 12/836,654, dated Sep. 28, 2012, 16 pages.
Office Action for U.S. Appl. No. 12/836,654, dated Mar. 1, 2013, 23 pages.
International Search Report for International Application No. PCT/US2010/042128, dated Aug. 27, 2010.
Written Opinion International Application No. PCT/US2010/042128, dated Aug. 27, 2010.
International Preliminary Report on Patentability for International Application No. PCT/US2010/042128, dated Jan. 17, 2012.
European Search Report for European Application No. 13173409.7, dated Sep. 16, 2013.
U.S. Appl. No. 14/457,412, filed Aug. 12, 2014 (now U.S. Pat. No. 9,539,146).
Office Action for U.S. Appl. No. 14/457,412, dated Mar. 25, 2016, 8 pages.
International Search Report and Written Opinion for International Patent Application No. PCT/US2015/044179, dated Dec. 18, 2015, 15 pages.
Office Action for U.S. Appl. No. 14/570,157, dated Jun. 15, 2016, 6 pages.
Office Action for U.S. Appl. No. 14/570,157, dated Jan. 20, 2016, 5 pages.
U.S. Appl. No. 13/800,113, filed Mar. 13, 2013.
U.S. Appl. No. 13/804,553, filed Mar. 14, 2013.
Office Action for U.S. Appl. No. 13/804,553, dated Apr. 20, 2015, 11 pages.
International Search Report and Written Opinion for International Application No. PCT/US2014/018320, dated Jun. 2, 2014, 10 pages.

(56) References Cited

OTHER PUBLICATIONS

Office Action for U.S. Appl. No. 13/804,612, dated Feb. 8, 2016, 6 pages.
International Search Report and Written Opinion for International Application No. PCT/US2014/018347, dated Apr. 17, 2014, 9 pages.
International Search Report and Written Opinion for International Application No. PCT/US2015/044173, dated Oct. 12, 2015, 9 pages.
Office Action for U.S. Appl. No. 14/456,080, dated May 18, 2016, 8 pages.
Office Action for U.S. Appl. No. 14/456,080, dated Dec. 22, 2016, 20 pages.
International Search Report and Written Opinion for International Application No. PCT/US2015/044177, dated Oct. 30, 2015, 10 pages.
Office Action for U.S. Appl. No. 14/457,266, dated May 18, 2016, 10 pages.
Office Action for U.S. Appl. No. 14/457,266, dated Dec. 22, 2016, 10 pages.
International Search Report and Written Opinion for International Application No. PCT/US2015/044183, dated Nov. 4, 2015, 9 pages.
Office Action for U.S. Appl. No. 14/457,293, dated Sep. 26, 2016, 9 pages.
Office Action for U.S. Appl. No. 14/457,293, dated Apr. 26, 2017, 11 pages.
International Search Report and Written Opinion for International Application No. PCT/US2015/044610, dated Nov. 5, 2015, 12 pages.
International Search Report for International Application No. PCT/US2009/069388, dated Jun. 30, 2010.
Written Opinion for International Application No. PCT/US2009/069388, dated Jun. 30, 2010.
U.S. Appl. No. 11/962,073, filed Dec. 20, 2007.
Comeau, M. et al., "Local Anesthesia of the Ear by Iontophoresis," vol. 98, Arch. Otolaryngol., pp. 114-120 (Aug. 1973).
Comeau, M. et al., "Anesthesia of the Human Tympanic Membrane by Iontophoresis of a Local Anesthetic," The Larynogoscope, vol. 88, pp. 277-285 (1978).
Echols, D. F. et al., "Anesthesia of the Ear by Iontophoresis of Lidocaine," Arch. Otolaryngol., vol. 101, pp. 418-421 (Jul. 1975).
Epley, J. M., "Modified Technique of Iontophoretic Anesthesia for Myringotomy in Children," Arch. Otolaryngol., vol. 103, pp. 358-360 (Jun. 1977).
Hasegawa, M. et al., "Iontophorectic anaesthesia of the tympanic membrane," Clinical Otolaryngoloy, vol. 3, pp. 63-66 (1978).
Ramsden, R. T. et al., "Anaesthesia of the tympanic membrane using iontophoresis," The Journal of Laryngology and Otology, 56(9):779-785 (Sep. 1977).
"Definition of Plenum," Compact Oxford English Dictionary [online], Retrieved from the Internet: <http://oxforddictionaries.com/definition/english/plenum>, Retrieved on Aug. 6, 2012, 2 pages.
"Definition of Plenum," Merriam-Webster's Online Dictionary, 11th Edition [online], Retrieved from the Internet: <http://www.merriam-webster.com/dictionary/plenum>, Retrieved on Aug. 14, 2012, 1 page.
Medtronic XOMED, "Activent® Antimicrobial Ventilation Tubes," Rev. 1.1, pp. 1-4, 2002, Jacksonville, FL.
Micromedics Innovative Surgical Products, "Micromedics Tympanostomy Tubes," [online], Retrieved on Jul. 15, 2010, Retrieved from the Internet <URL: http://www.micromedics-usa.com/products/otology/micromedicstubes.htm>, 7 pages.
Armstrong, "A New Treatment for Chronic Secretory Otitis Media" A.M.A. Archives of Otolaryngology, pp. 653-654 (1954).
Feuerstein, "A Split-Tube Prosthesis in Serous Otitis Media" Sixty-ninth Annual Session of the American Academy of Ophthalmology and Otolaryngology, Oct. 18-23, 1964, Chicago, IL, pp. 343-344.
Jurgens. et al., "Three New Middle Ear Ventilation Tubes" Seventy-sixth Annual Session of the American Academy of Ophthalmology and Otolaryngology, Sep. 20-24, 1971, Las Vegas, NV, pp. 1017-1019 (1971).
Lindeman et al., The "Arrow Tube" Residents in Otolaryngology, Massachusetts Eye and Ear Infirmary, 1 page (1964).
Pappas, "Middle Ear Ventilation Tubes" Meeting of the Southern Section of the American Laryngological, Rhinological and Otological Society, Inc., Williamsburg, VA, Jan. 12, 1974, pp. 1098-1117.
Per-Lee, "A Wide Flanged Middle Ear Ventilation Tube" Seventy-first Annual Session of the American Academy of Ophthalmology and Otolaryngology, Oct. 16-21, 1966, Chicago, IL, pp. 358-359.
Reuter, "The Stainless Bobbin Middle Ear Ventilation Tube" Seventy-second Annual Session of the American Academy of Ophthalmology and Otolaryngology, Oct. 29-Nov. 3, 1967, Chicago, IL, pp. 121-122.
Ringenberg, "A New Middle Ear Ventilation Device" Seventy-second Annual Session of the American Academy of Ophthalmology and Otolaryngology, Oct. 29-Nov. 3, 1967, Chicago, IL, 1 page.
Schmidt et al. "Transtympanic Aeration of the Middle Ear With Blocked Eustachian Tube" Acta Otolaryng., pp. 277-282 (1965).
Sheehy, "Collar Button Tube for Chronic Serous Otitis" Sixty-eighth Annual Session of the American Academy of Ophthalmology and Otolaryngology, Oct. 20-25, 1963, New York, NY, pp. 888-889.
Santa Barbara Medco, Inc. "Otological Ventilation Tubes" Product Brochure from http://www.sbmedco.com/ptfe_shepard.asp, 8 pages (Feb. 11, 2001).
Rhinology Products, Boston Medical Products, www.bosmed.com [date of publication unknown], pp. 1-16.

\* cited by examiner

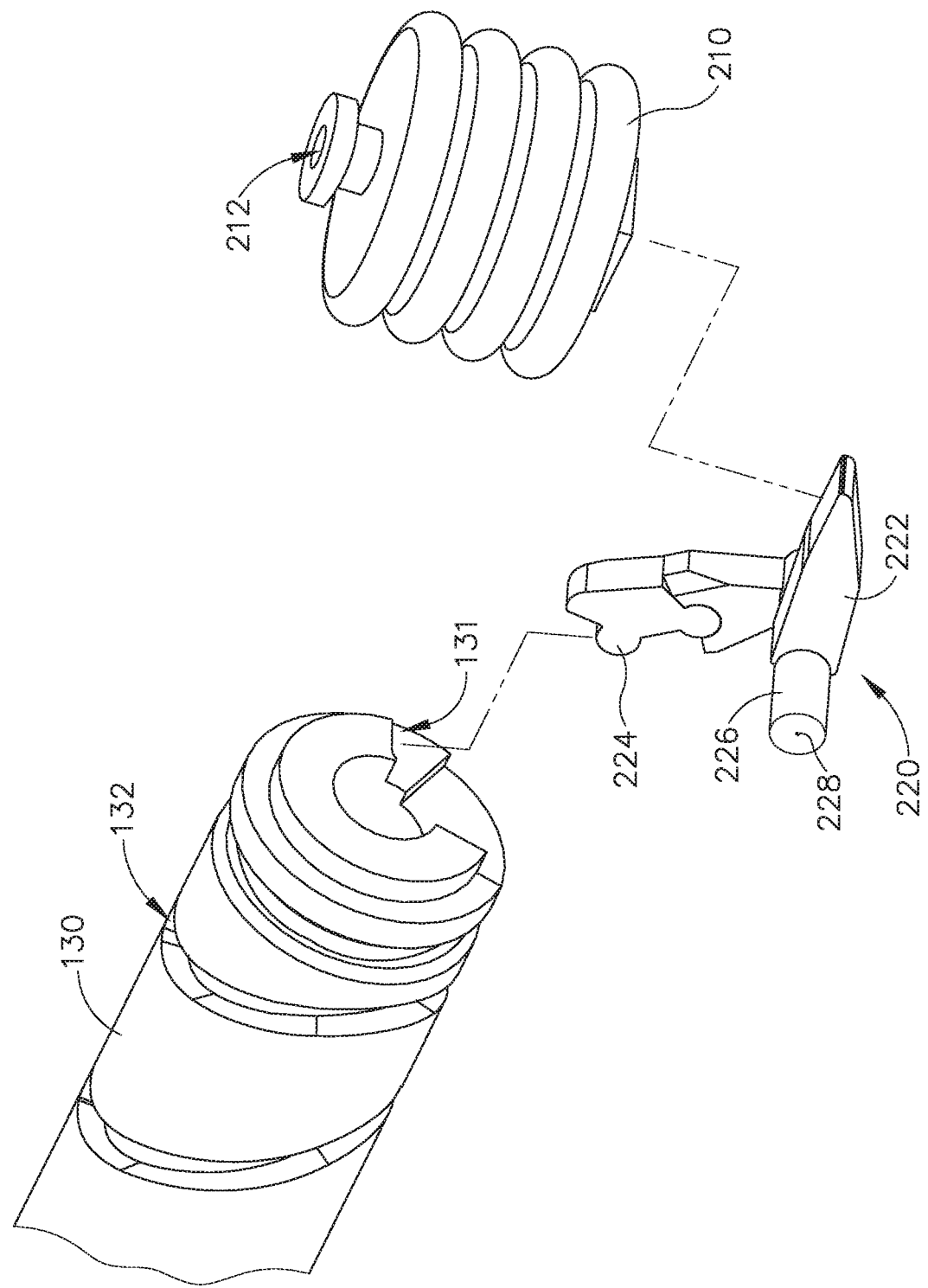

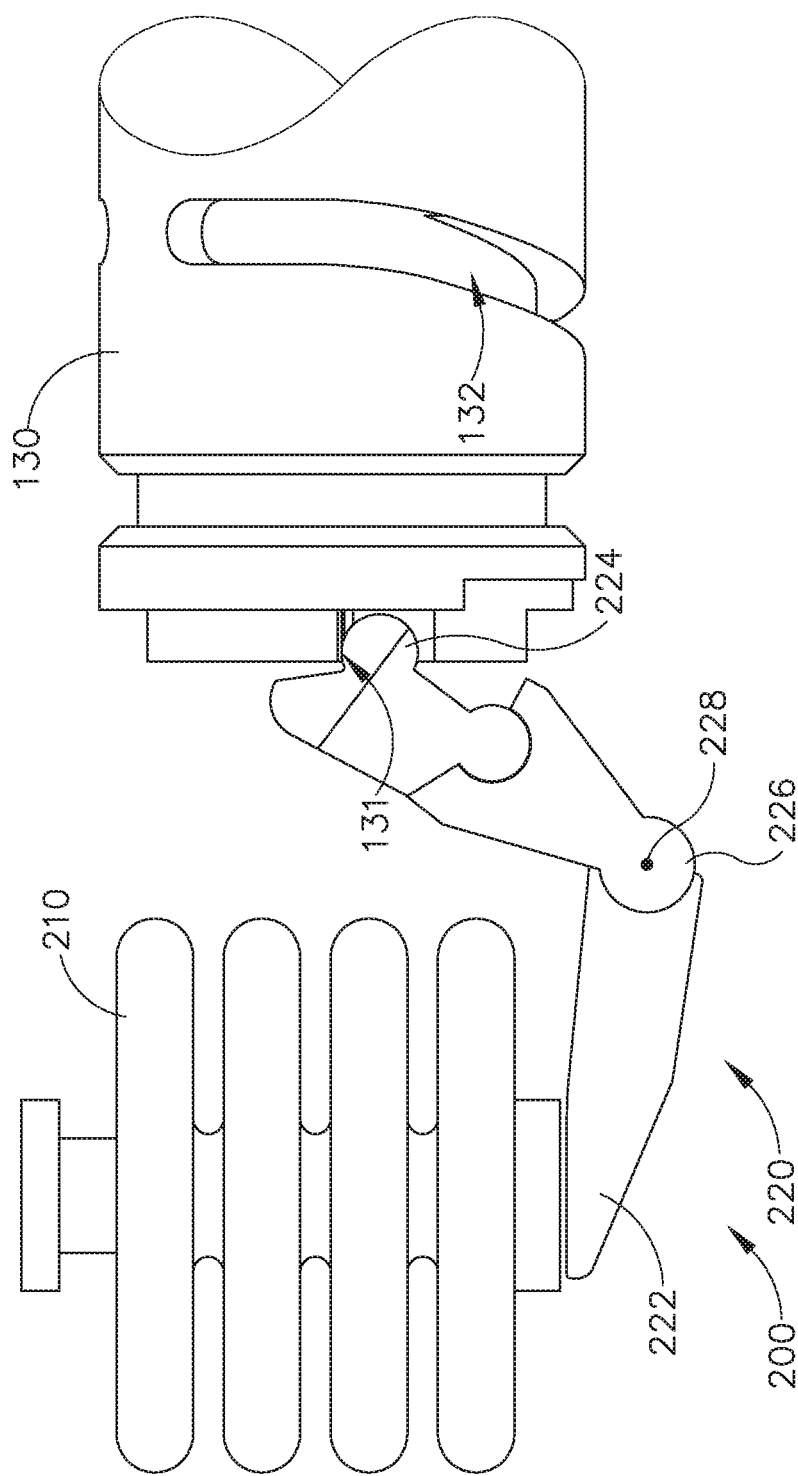

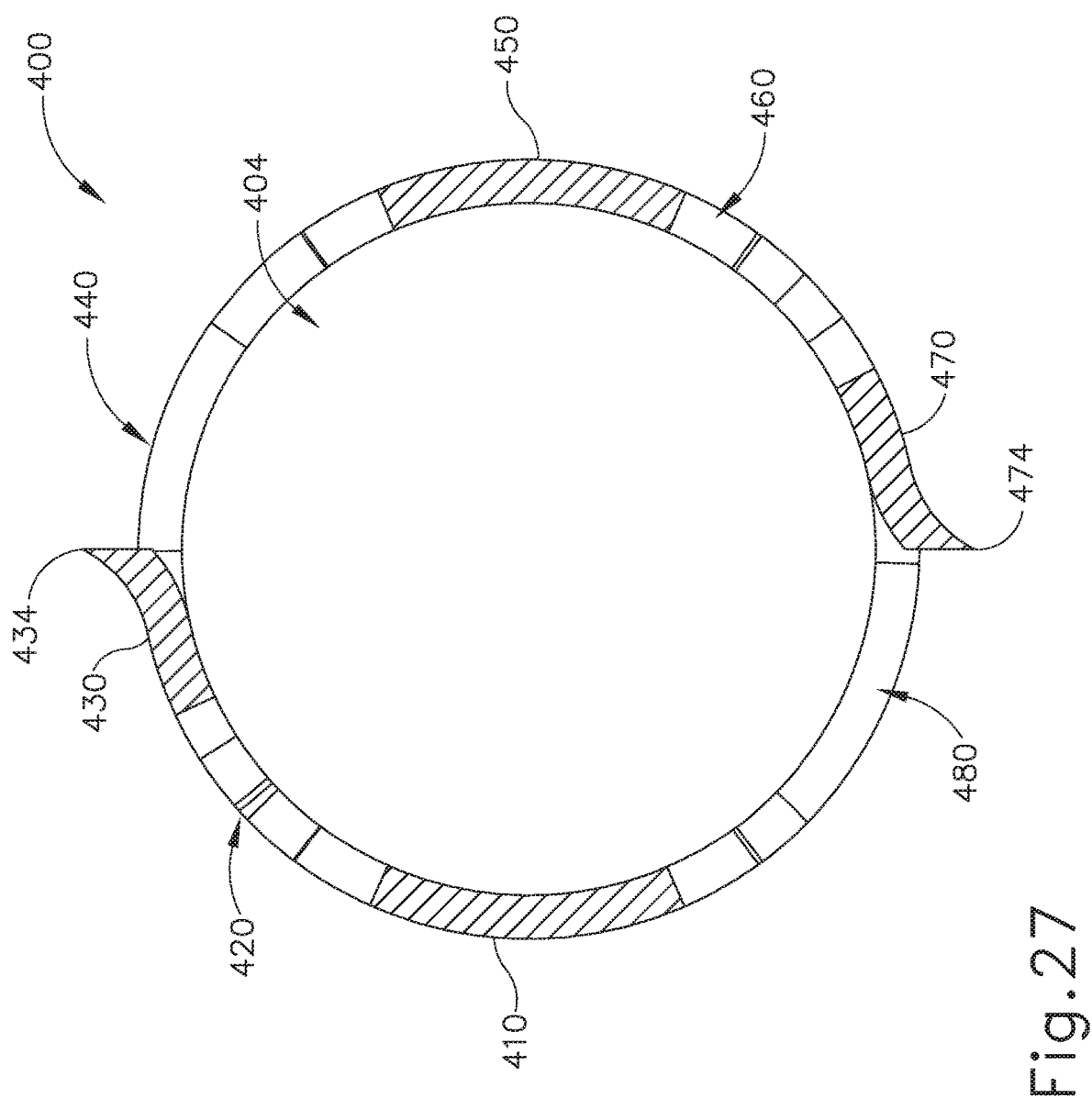

TYMPANOSTOMY TUBE DELIVERY DEVICE WITH CUTTING DILATOR

RELATED APPLICATION

This application is a continuation of U.S. patent application Ser. No. 13/804,612, entitled "TYMPANOSTOMY TUBE DELIVERY DEVICE WITH CUTTING DILATOR," filed on Mar. 14, 2013, the contents of which are herein incorporated by reference in its entirety.

BACKGROUND

Some children may exhibit recurrent episodes of otitis media and/or -otitis media with effusion. Treatment of severe cases may involve the placement of a pressure equalization tube or tympanostomy tube through the tympanic membrane to provide adequate drainage of the middle ear by providing fluid communication between the middle and outer ear. In particular, such a tube may provide a vent path that promotes drainage of fluid from the middle ear via the Eustachian tube and may thus reduce stress imposed on the tympanic membrane from pressure within the middle ear. This may further reduce the likelihood of future infections and pressure induced ruptures of the tympanic membrane. Pressure equalization tubes may fall out spontaneously within about a year of placement. Exemplary pressure equalization tube delivery systems are disclosed in U.S. Pat. No. 8,052,693, entitled "System and Method for the Simultaneous Automated Bilateral Delivery of Pressure Equalization Tubes," issued Nov. 8, 2011, the disclosure of which is incorporated by reference herein. Additional exemplary pressure equalization tube delivery systems are disclosed in U.S. Pat. No. 8,249,700, entitled "System and Method for the Simultaneous Bilateral Integrated Tympanic Drug Delivery and Guided Treatment of Target Tissues within the Ears," issued Aug. 21, 2012, the disclosure of which is incorporated by reference herein. Still additional exemplary pressure equalization tube delivery systems are disclosed in U.S. Pub. No. 2011/0015645, entitled "Tympanic Membrane Pressure Equalization Tube Delivery System," published Jan. 20, 2011, the disclosure of which is incorporated by reference herein.

Insertion of a pressure equalization tube may be performed using general anesthesia in some cases, which may require additional resources such as an operating room, the presence of an anesthesiologist, and time in a recovery room. Furthermore, the use of general anesthesia may include certain risks that a patient may or may not be comfortable with undertaking. Some pressure equalization tube delivery systems and methods provide a local anesthetic through iontophoresis. Examples of such systems and methods are disclosed in U.S. Pub. No. 2010/0198135, entitled "Systems and Methods for Anesthetizing Ear Tissue," published Aug. 5, 2010, the disclosure of which is incorporated by reference herein. Additional examples of such systems and methods are disclosed in U.S. Pat. No. 8,192,420, entitled "Iontophoresis Methods," issued Jun. 5, 2012, the disclosure of which is incorporated by reference herein.

While a variety of pressure equalization tube delivery systems and methods have been made and used, it is believed that no one prior to the inventor(s) has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 10 depicts an exploded perspective view of a trip mechanism of the actuation features of FIG. 3;

FIG. 11A depicts a side elevational view of the trip mechanism of FIG. 10, with a lever engaging a camshaft;

FIG. 27 depicts a cross-sectional view of the dilator tube of FIG. 19, taken along line 27-27 of FIG. 25.

Figure 1:
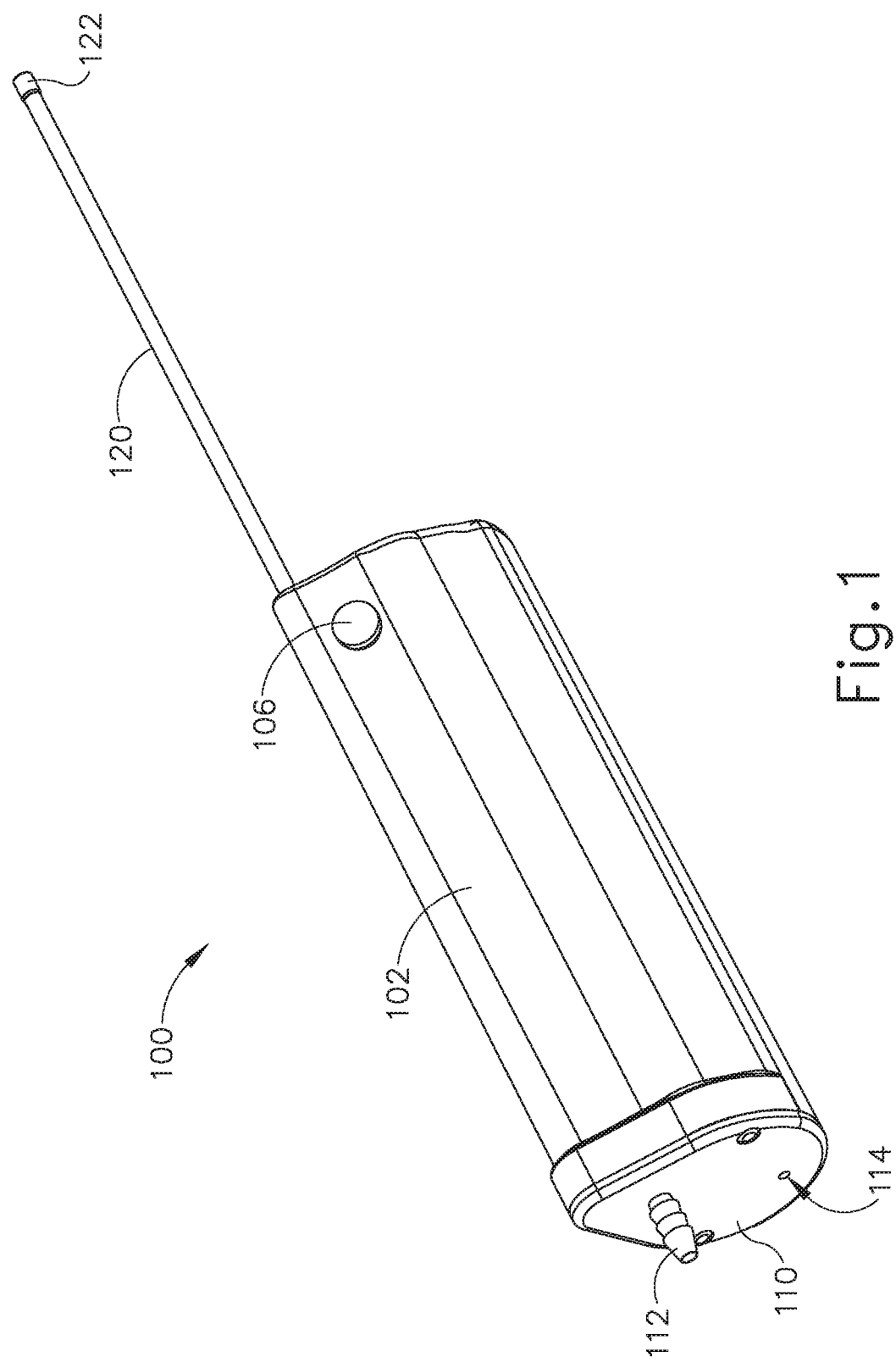
FIG. 1 depicts a perspective view of an exemplary pressure equalization tube delivery device (PETDD)

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Tympanic Tube Delivery Instrument

As noted above, a pressure equalization (PE) tube may be delivered to the tympanic membrane (TM) of a patient as a way of treating, for example, otitis media. In some instances, a delivery instrument may be used to insert PE tubes in the tympanic membrane (TM) without the use of general anesthesia. FIG. 1 shows an exemplary equalization tube delivery device (PETDD) (100) that may be used in such procedures. It should be understood that PETDD (100) may be used with an endoscope to provide visualization of the tympanic membrane (TM) during use of PETDD (100). It should also be understood that a patient may receive local anesthesia at the tympanic membrane (TM) through a process of iontophoresis before PETDD (100) is actuated to deploy a PE tube. By way of example only, such iontophoresis may be provided in accordance with at least some of the teachings of U.S. Pub. No. 2010/0198135, the disclosure of which is incorporated by reference herein; and/or in accordance with at least some of the teachings of U.S. Pat. No. 8,192,420, the disclosure of which is incorporated by reference herein. Other suitable ways in which PETDD (100) may be used will be apparent to those of ordinary skill in the art in view of the teachings herein.

As shown in FIG. 1, PETDD (100) of this example comprises a housing (102), a rear plate (110), and a cannula (120) extending distally from housing (102). Housing (102) is configured to be handheld, such that an operator may fully operate PETDD (100) using a single hand. Rear plate (110) includes a vacuum port (112) and a vent port (114). In the present example, vacuum port (112) is in the form of a barbed nib that is configured to couple with a conventional flexible tube; while vent port (114) is simply an opening formed through rear plate (110). Other suitable configurations for ports (112, 114) will be apparent to those of ordinary skill in the art in view of the teachings herein. Cannula (120) of the present example comprises an elongate tube having a clear tip (122) at the distal end of cannula (120). Clear tip (122) is configured to contact a patient's tympanic membrane (TM) while enabling visualization of the distal end of cannula (120). Other than vacuum port (112), rear plate (110) is hermetically sealed relative to housing (102). The interface between cannula (120) and housing (102) is also hermetically sealed. Thus, the interior of housing (102) defines a fluid tight hollow interior that is in fluid communication with vacuum port (112) and an interior region of cannula (120), where "fluid" in the context of this description includes compressible fluid such as air.

Figure 2:
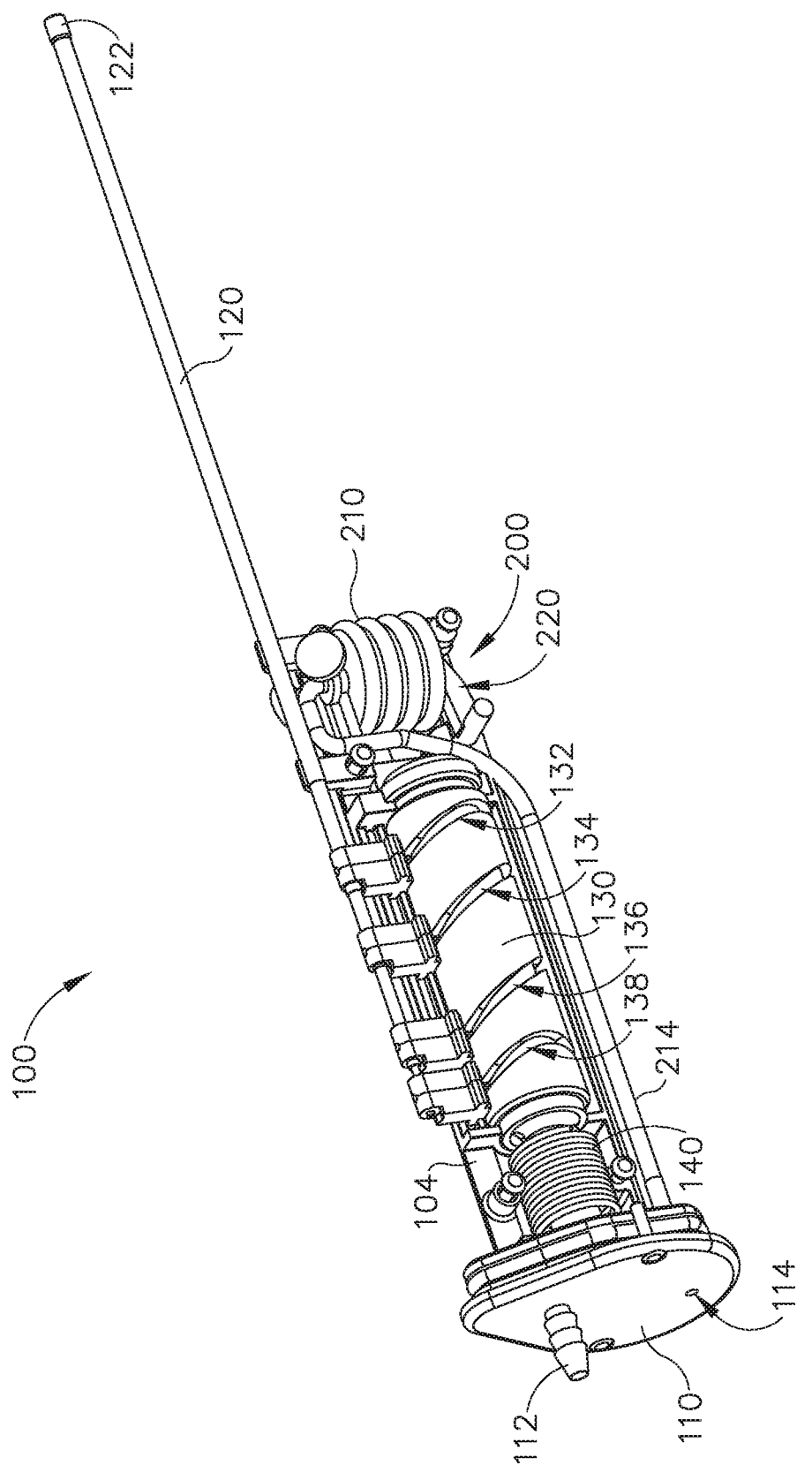
FIG. 2 depicts a perspective view of the PETDD of FIG. 1, with the housing omitted and a chassis half omitted.

As shown in FIG. 2, a chassis (104) is coupled with housing (102) and supports several components within housing (102). In the present example, a second chassis (not shown) is coupled with chassis (104) and is structurally substantially identical from chassis (104), but is omitted from FIG. 2 just to enable viewing of features that would otherwise be obscured by the second chassis. As can be seen in FIG. 2, chassis (104) supports a camshaft (130) and a trip mechanism (200). Camshaft (130) includes a dilator track (132), a shield tube track (134), a pusher track (136), and a piercer track (138). Tracks (132, 134, 136, 138) are formed as recesses in camshaft (130) and each track (132, 134, 136, 138) has a unique configuration in order to provide a particular sequence of operation of translating components as will be described in greater detail below. A torsion spring (140) is coupled to the proximal end of camshaft (130). Torsion spring (140) is also grounded against the distal face of rear plate (110). Torsion spring (140) resiliently provides a rotational bias to camshaft (130). In particular, torsion spring (140) urges camshaft (130) to rotate in the clockwise direction (viewed from the distal end of PETDD (100) toward the proximal end of PETDD (100)) about the longitudinal axis of camshaft (130). As will be described in greater detail below (200), trip mechanism selectively resists such rotation. While torsion spring (140) is used to bias camshaft (130) in the present example, it should be understood that any other suitable types of components may be used to bias camshaft (130).

Figure 3:
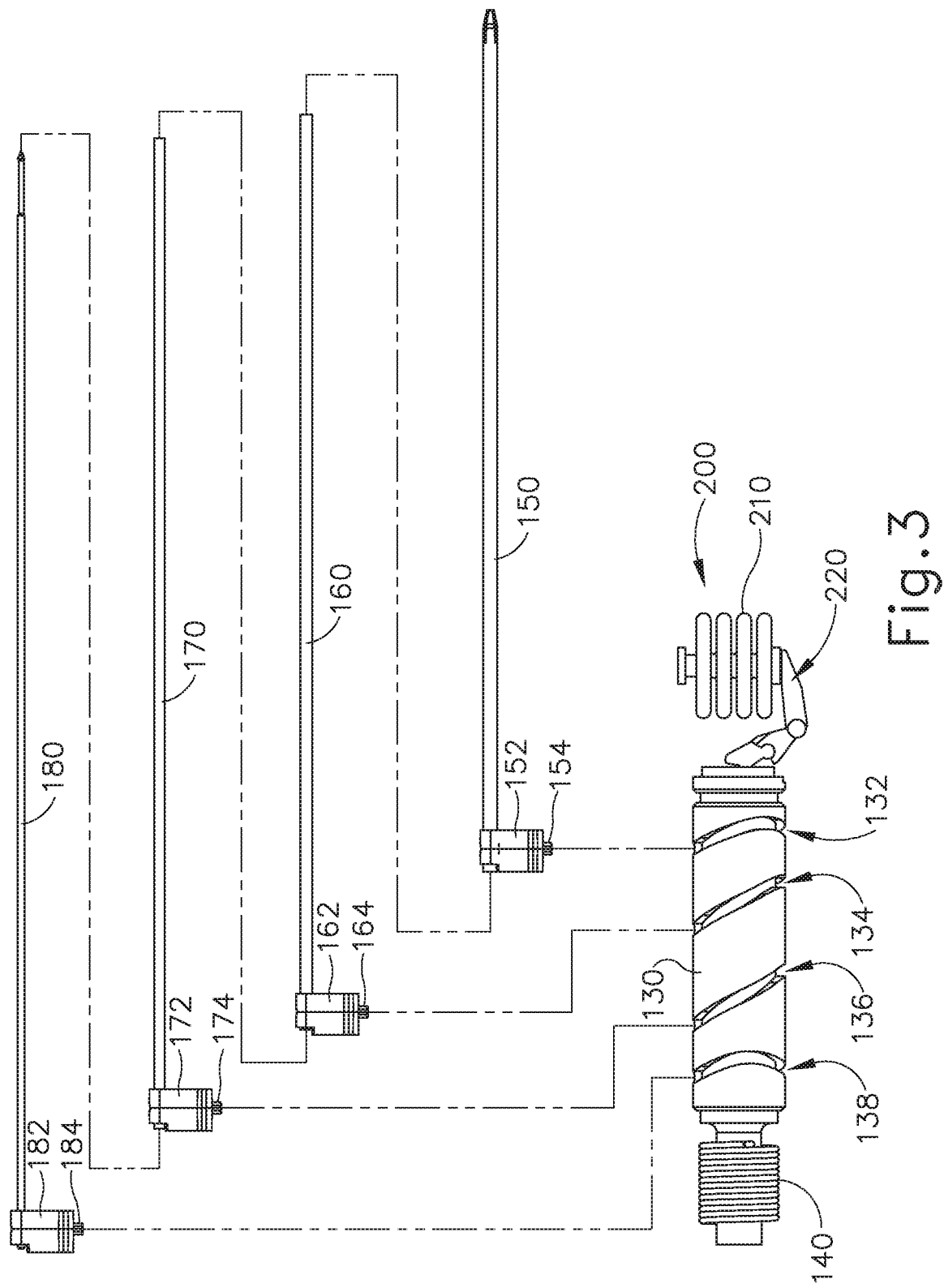
FIG. 3 depicts an exploded elevational view of actuation features of the PETDD of FIG. 1.

As shown in FIG. 3, various components are engaged with camshaft (130) and are thereby actuated by rotation of camshaft (130). In particular, a dilator tube (150), a shield tube (160), a pusher tube (170), and a piercer (180) are all engaged with camshaft (130). Tubes (150, 160, 170) and piercer (180) are all coaxially disposed within cannula (120). Piercer (180) is coaxially and slidably disposed within pusher tube (170), which is coaxially and slidably disposed within shield tube (160), which is coaxially and slidably disposed within dilator tube (150), which is coaxially and slidably disposed within cannula (120). Tubes (150, 160, 170) and piercer (180) all translate relative to cannula (120) in a particular sequence in order to deploy a PE tube as will be described in greater detail below. This sequence is driven by rotation of camshaft (130).

A cam follower (152) is fixedly secured to the proximal end of dilator tube (150). Cam follower (152) includes a laterally projecting pin (154) that is disposed in dilator track (132), such that rotation of camshaft (130) causes cam follower (152) and dilator tube (150) to translate. Similarly, a cam follower (162) is fixedly secured to the proximal end of shield tube (160). Cam follower (162) includes a laterally projecting pin (164) that is disposed in shield tube track (134), such that rotation of camshaft (130) causes cam follower (162) and shield tube (160) to translate. A cam follower (172) is fixedly secured to the proximal end of pusher tube (170). Cam follower (172) includes a laterally projecting pin (174) that is disposed in pusher tube track (136), such that rotation of camshaft (130) causes cam follower (172) and pusher tube (170) to translate. Finally, a cam follower (182) is fixedly secured to the proximal end of piercer (180). Cam follower (182) includes a laterally projecting pin (184) that is disposed in piercer track (138), such that rotation of camshaft (130) causes cam follower (182) and piercer (180) to translate.

Figure 4:
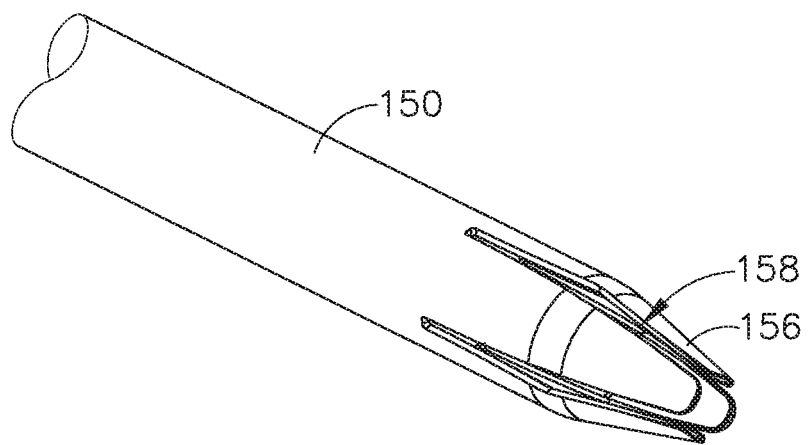
FIG. 4 depicts a perspective view of the distal end of a dilator of the actuation features of FIG. 3.
Figure 5:
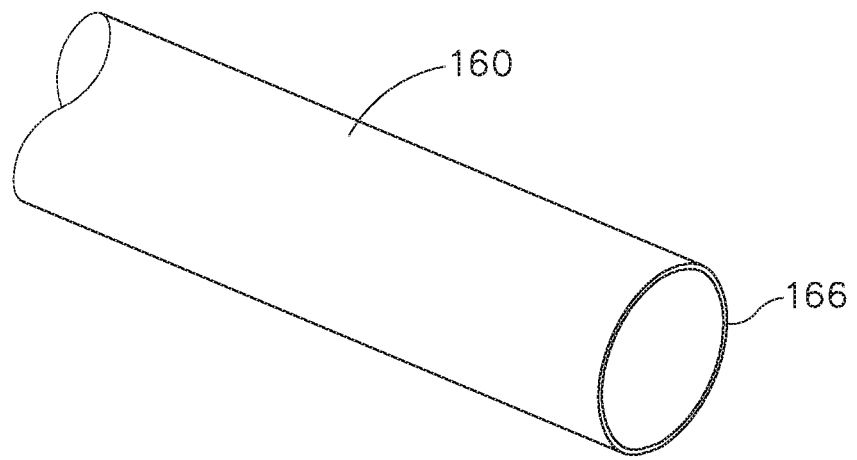
FIG. 5 depicts a perspective view of the distal end of a shield tube of the actuation features of FIG. 3.
Figure 6:
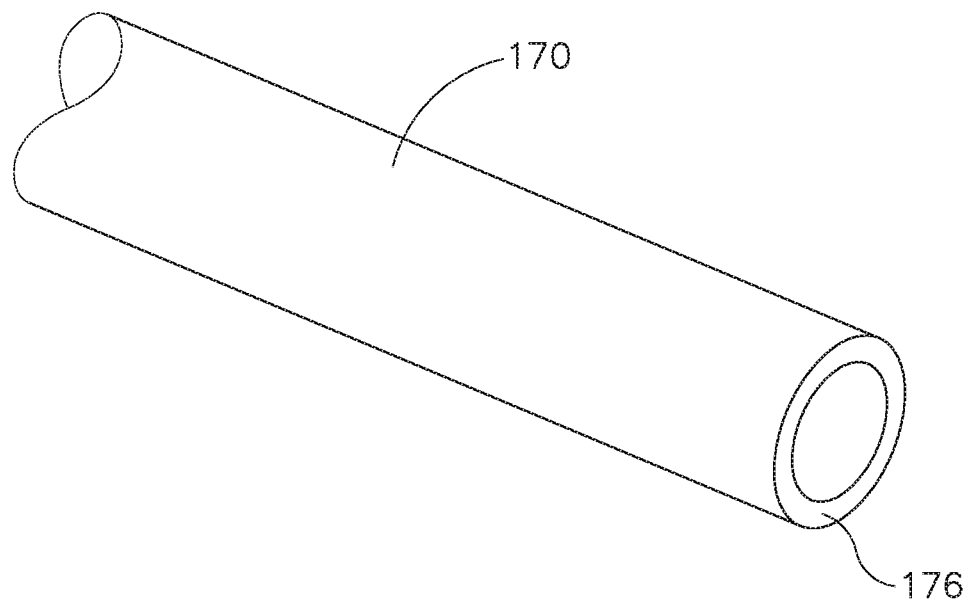
FIG. 6 depicts a perspective view of the distal end of a pusher of the actuation features of FIG. 3.
Figure 7:
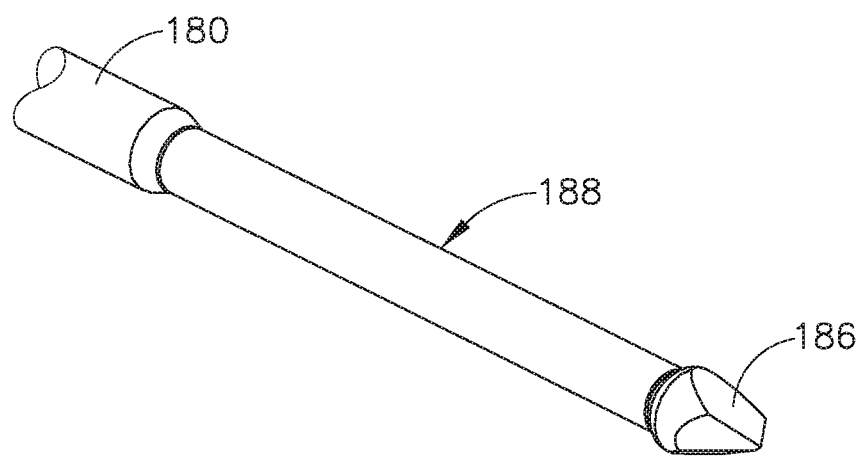
FIG. 7 depicts a perspective view of the distal end of a piercer of the actuation features of FIG. 3.

As shown in FIG. 4, the distal end of dilator tube (150) includes a plurality of generally flexible leaves (156) that are separated by longitudinally extending gaps (158). Leaves (156) are resiliently biased to assume the inwardly deflected positioning shown in FIG. 4; but are operable to flex outwardly from this positioning as will be described in greater detail below. As shown in FIG. 5, the distal end of shield tube (160) simply includes a circular edge (166). As shown in FIG. 6, the distal end of pusher tube (170) includes a distal face (176). In the present example, the difference between the inner diameter of pusher tube (170) and the outer diameter of pusher tube (170) is greater than the difference between the inner diameter of shield tube (160) and the outer diameter of shield tube (160). Thus, distal face (176) presents a more prominent contact surface than circular edge (166). As shown in FIG. 7, the distal end of piercer (180) includes a sharp, multi-faceted tip (186) that is configured to pierce through a patient's tympanic membrane (TM). In the present example, piercer (180) also includes a neck-down region (188) having a reduced diameter.

Figure 8:
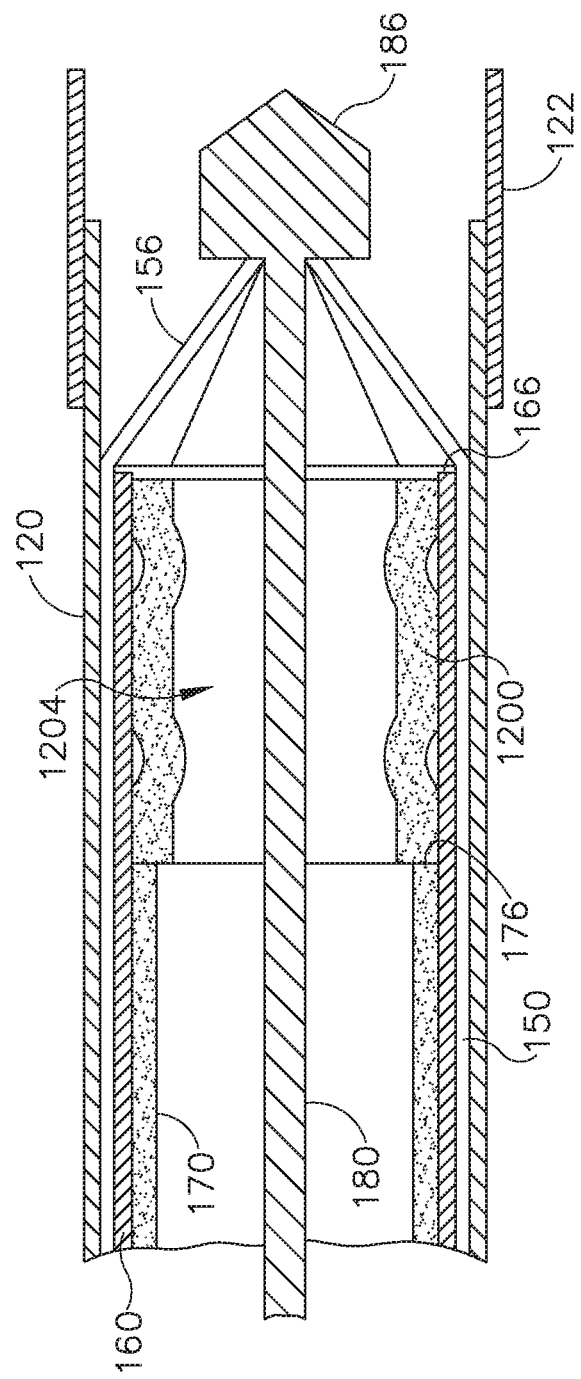
FIG. 8 depicts a cross-sectional side view of the actuation features of FIG. 3 with an exemplary pressure equalization (PE) tube.
Figure 13:
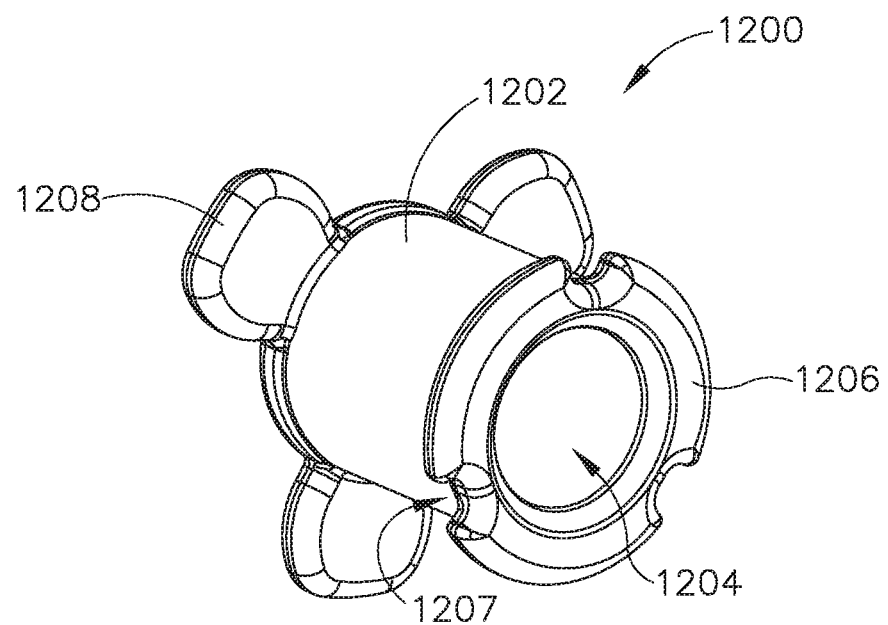
FIG. 13 depicts a perspective view of the proximal side of an exemplary PE tube suitable for delivery by the PETDD of FIG. 1.
Figure 14:
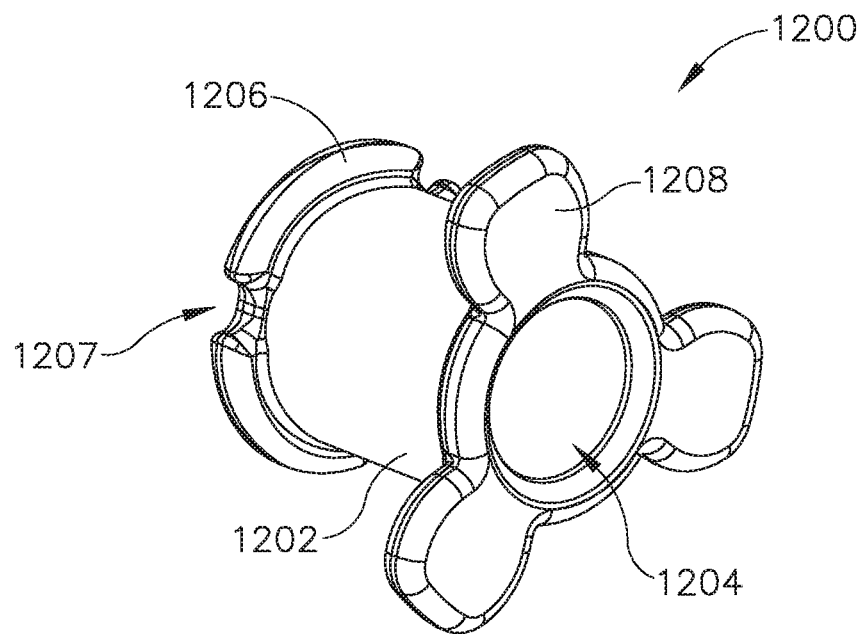
FIG. 14 depicts a perspective view of the distal side of the PE tube of FIG. 13.
Figure 15:
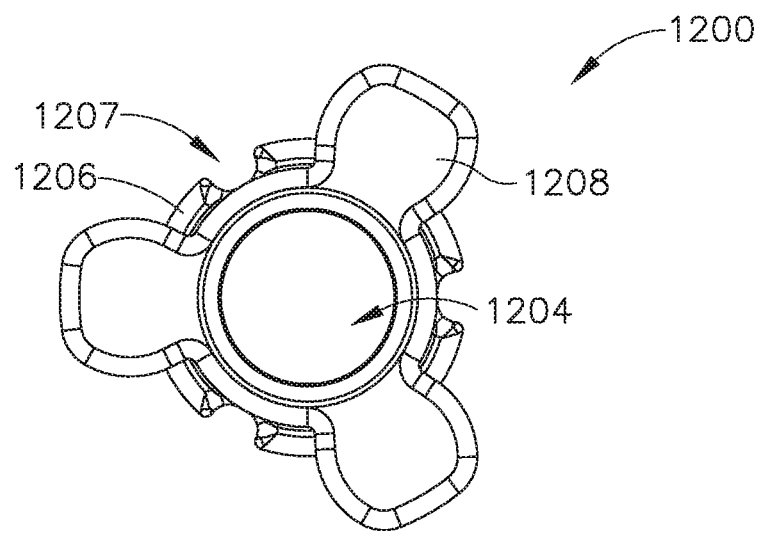
FIG. 15 depicts a distal elevational view of the PE tube of FIG. 13.
Figure 16:
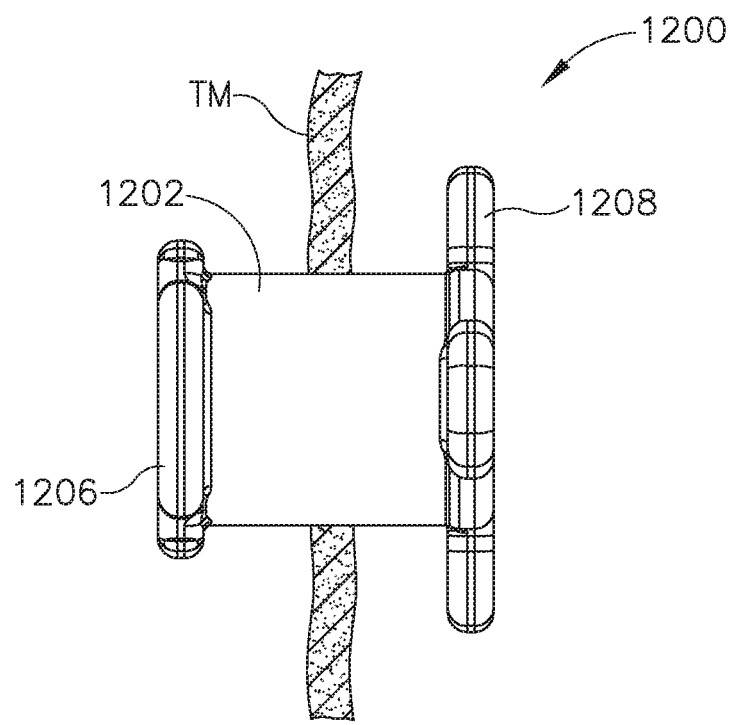
FIG. 16 depicts a side elevational view of the PE tube of FIG. 13, positioned within a tympanic membrane.

FIG. 8 shows the positioning of tubes (150, 160, 170), piercer (180), and PE tube (1200) within cannula (120) before camshaft (130) starts rotating from a home position. As shown, tip (186) of piercer (180) is positioned distal to leaves (156) of dilator tube (150), such that leaves (156) are positioned about neck-down region (188) of piercer (180). PE tube (1200) is positioned within the distal end of shield tube (160), whose distal edge (166) is just proximal to leaves (156). Pusher tube (170) is proximal to PE tube (1200), with distal face (176) of pusher tube (170) abutting the proximal end of PE tube (1200). In the present example, PE tube (1200) is resiliently biased to assume a rivet-like shape presenting a distal flange (1208) and a proximal flange (1206) (see FIG. 13). However, PE tube (1200) is compressed against this bias, thereby assuming a generally cylindraceous configuration, when PE tube (1200) is disposed within shield tube (160) as shown in FIG. 8.

Figure 9:
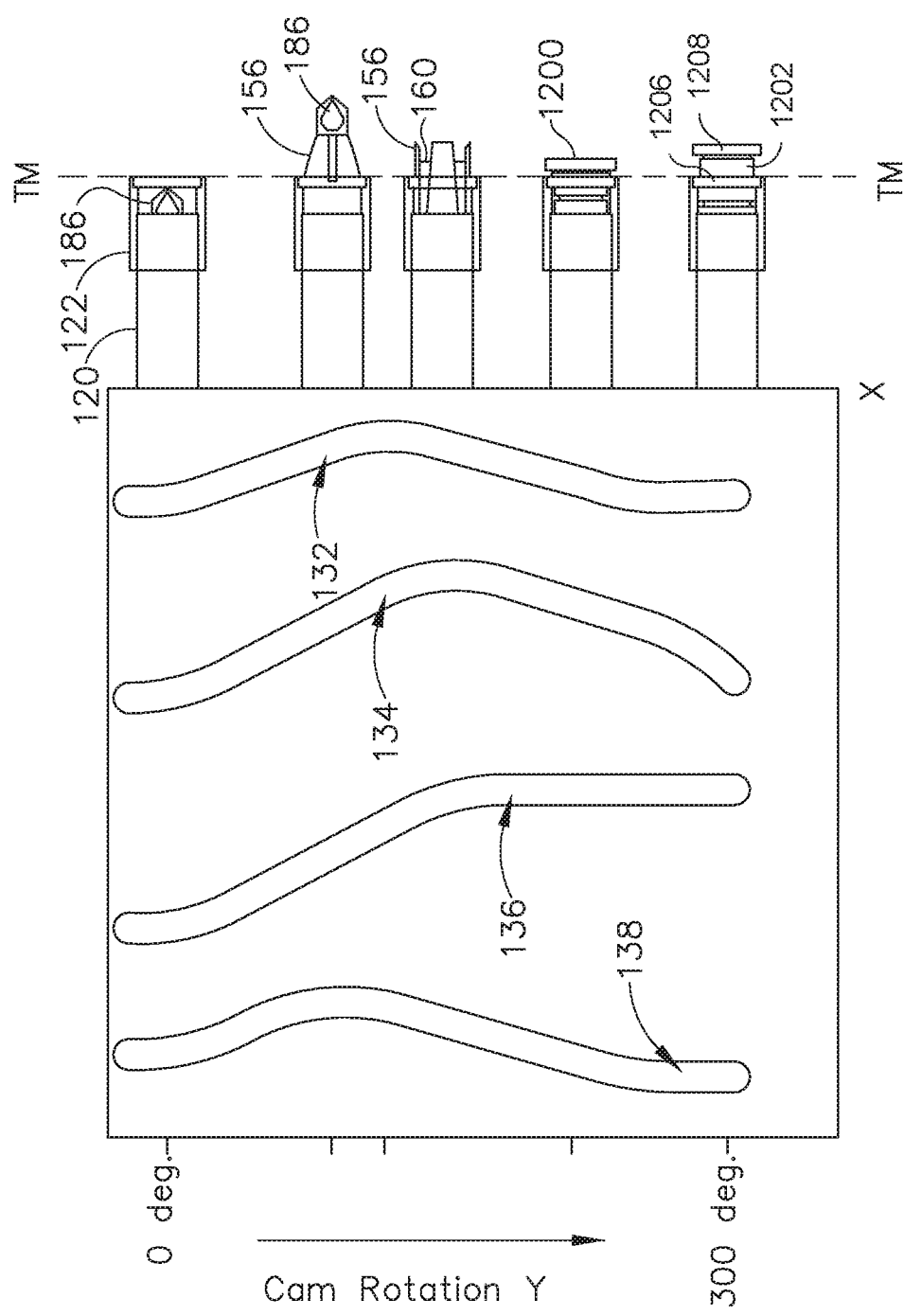
FIG. 9 depicts a displacement and operational diagram associated with the actuation features of FIG. 3.

FIG. 9 depicts a sequence of operation that occurs upon rotation of camshaft (130) from a home position to an actuated position, where tracks (132, 134, 136, 138) are shown developed into a flat pattern for purpose of illustration. The sequence starts at the top region of FIG. 9, which shows the distal end of clear tip (122) contacting the patient's tympanic membrane (TM). At this stage, tubes (150, 160, 170), piercer (180), and PE tube (1200) are at the positions shown in FIG. 8. Once camshaft (130) starts rotating at the urging of torsion spring (140), pins (154, 164, 174, 184) begin to ride along their respective tracks (132, 134, 136, 138), such that piercer tip (186) and leaves (156) are driven distally through the tympanic membrane (TM). While not directly shown in FIG. 8, it should be understood that tubes (160, 170, 190) are also driven distally during this transition, though tubes (160, 170, 190) remain proximal to clear tip (122) at this stage. As camshaft (130) continues to rotate, piercer (180) begins retracting proximally while tubes (160, 170, 190) continue to advance distally. As shown, shield tube (160) spreads leaves (156) outwardly from their default positions. This further dilates the puncture site in the tympanic membrane (TM). Shield tube (160) continues to contain PE tube (1200) at this stage. As camshaft (130) continues to rotate, piercer (180) and dilator (150) retract proximally behind clear tip (122). Shield tube (160) also begins to retract proximally, while pusher tube (170) remains longitudinally stationary. This relative movement uncovers the distal end of PE tube (1200), such that the resilient bias of PE tube (1200) is allowed to form distal flange (192) on the far side of the tympanic membrane (TM). Piercer (180) eventually returns to the fully proximal position, dilator (170) eventually returns to the fully proximal position, and pusher tube (170) eventually reaches a fully distal position. As camshaft (130) continues to rotate, shield tube (160) continues to retract proximally while pusher tube (170) remains longitudinally stationary. This relative movement uncovers the proximal end of PE tube (1200), such that the resilient bias of PE tube (1200) is allowed to form proximal flange (194) on the near side of the tympanic membrane (TM).

Upon completion of the above described sequence shown in FIG. 9, cannula (120) is withdrawn from the patient's ear, leaving the actuated PE tube (1200) in place in the patient's the tympanic membrane (TM). Flanges (192, 194) maintain the position of PE tube (1200) in TM, while the passageway formed by the interior (196) of PE tube (1200) (see FIG. 8) provides a path for fluid communication between the patient's inner ear and outer ear. This fluid path further provides pressure equalization between the patient's inner ear and outer ear.

As noted above, PETDD (100) of the present example includes a vacuum port (112) that is operable to couple with a vacuum source (not shown). As also noted above, this vacuum port (112) is in fluid communication with the interior of housing (102), which is further in fluid communication with cannula (120). It should be understood that cannula (120) and/or one of the tubes (150, 160, 170) within cannula (120) may provide a path for fluid communication between the interior of housing (102) and tip (122). By way of example only, such a path may be formed by a gap between the outer diameter of dilator tube (150) and the inner diameter of cannula (120). In addition or in the alternative, such a path may be formed through the interior of pusher tube (170), through interior (196) of PE tube (1200), and through gaps (158) between leaves (156) of dilator (150). Other suitable ways for providing a path for fluid communication between the interior of housing (102) and tip (122) will be apparent to those of ordinary skill in the art in view of the teachings herein. Regardless of how the path is formed, it should be understood that the path may be used to communicate a vacuum to tip (122), which may assist in drawing the tympanic membrane (TM) toward tip (122). For instance, an operator may make an initial contact between tip (122) and TM, then activate a vacuum source that is in communication with port (112) to communicate a vacuum to tip (122), thereby completing full contact between tip (122) and the tympanic membrane (TM). Such vacuum assisted contact may reduce risks that may be associated with operator error when the operator fails to achieve sufficient contact between tip (122) and the tympanic membrane (TM).

Figure 11B:
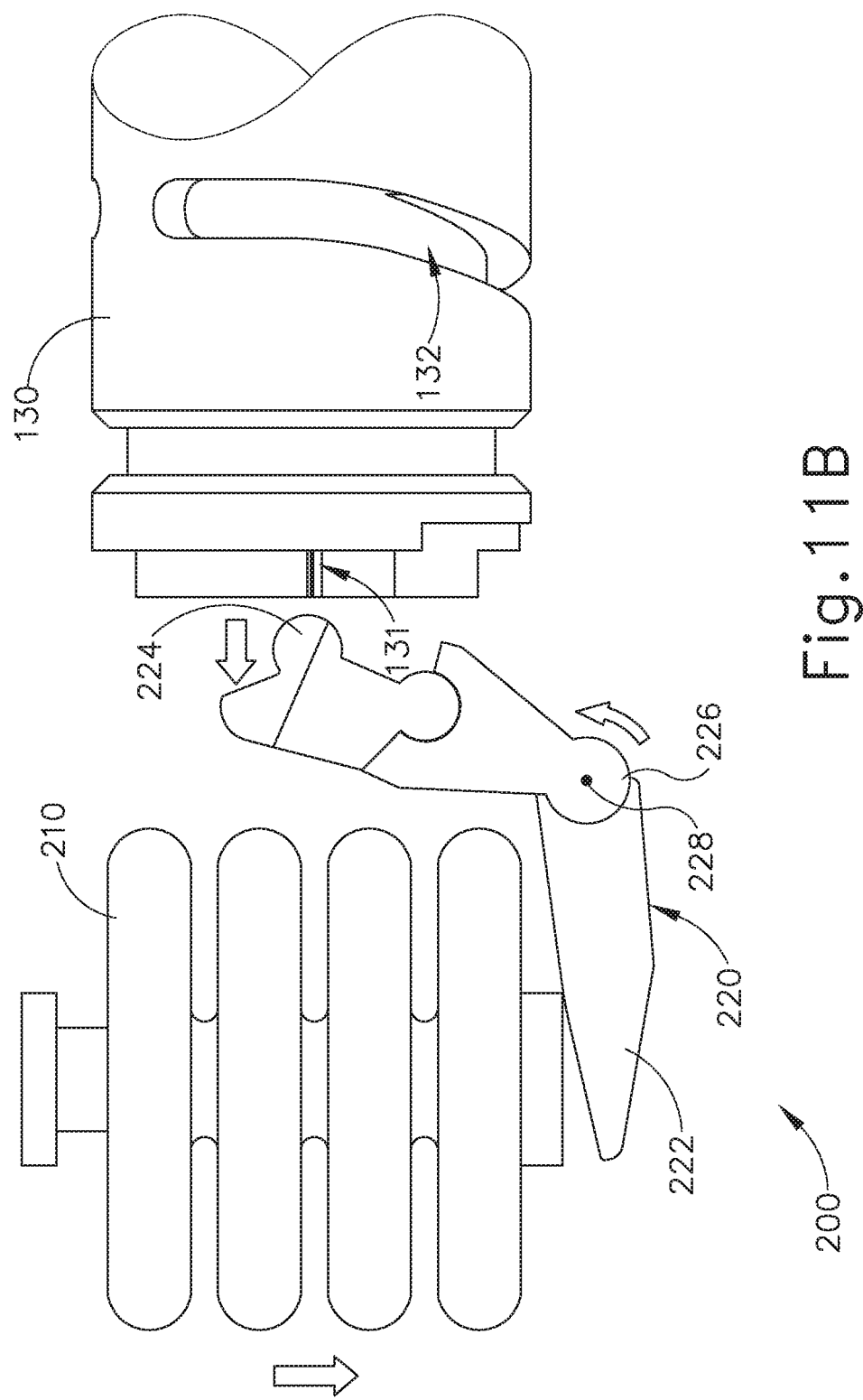
FIG. 11B depicts a side elevational view of the trip mechanism of FIG. 10, with the lever disengaged from the camshaft.

As also noted above, PETDD (100) of the present example includes a trip mechanism (200) that is configured to selectively resist rotation of camshaft (130) by torsion spring (140). As best seen in FIGS. 10-11, trip mechanism (200) of this example comprises an expandable bellows (210) and a pivoting member (220). Bellows (210) includes a fluid port (212) that is coupled with vent port (114) of rear plate (110) via a vent tube (214) (see FIG. 2). Bellows (210) is expandable from a compressed configuration (FIG. 11A) to an expanded configuration (FIG. 11B). Pivoting member (220) includes a lever arm (222), a catch arm (224), and a pivot pin (226). Pivot pin (226) is pivotally supported by chassis (104) and defines a pivot axis (228). Lever arm (222) is positioned underneath bellows (210). Catch arm (224) is configured to selectively engage a catch feature (131) of camshaft (130). In particular, when pivoting member (220) is in a first position as shown in FIG. 11A, catch arm (224) is engaged with catch feature (131) of camshaft (130). This engagement presents camshaft (130) from rotating under the influence of torsion spring (140). When pivoting member (220) is in a second position as shown in FIG. 11B, catch arm (224) is disengaged from catch feature (131) of camshaft (130), enabling camshaft (130) to rotate under the influence of torsion spring (140) to provide the sequence of operation described above.

Trip mechanism (200) of the present example automatically transitions from a first position (FIG. 11A) to a second position (FIG. 11B) when a certain level of vacuum is achieved within the interior of housing (102). During an exemplary use of PETDD (100), tip (122) is positioned adjacent to a patient's tympanic membrane (TM) and then a vacuum source communicates a vacuum to tip (122) via port (112), the interior of housing (102), and components between housing (102) and tip (122). Before tip (122) reaches full contact with TM, the pressure within the interior of housing (102) may reduce slightly. However, once tip (122) reaches full contact with the tympanic membrane (TM) (e.g., due to suction drawing the tympanic membrane (TM) against tip (122)), the pressure within the interior of housing (102) will drop significantly. This pressure drop will be encountered by the exterior of bellows (210), while the interior of bellows (210) remains in fluid communication with atmospheric air via port (114). Bellows (210) will thus experience a pressure differential that will cause bellows (210) to expand from the position shown in FIG. 11A to the position shown in FIG. 11B.

It should be understood from the foregoing that a vacuum may be used to assist in achieving full apposition between tip (122) of cannula (120) and TM; and that once such apposition is achieved, trip mechanism (200) may effectively unlock camshaft (130) to thereby automatically trigger a PE tube (1200) deployment sequence.

In some versions, housing (102) also includes one or more lateral vent ports (106) that are positioned to be selectively covered or otherwise closed by the hand of the operator that is grasping housing (102). While FIG. 1 shows a single vent port (106), it should be understood that one or more additional vent ports (106) may be provided. In versions having a user actuated vent port (106), vent port (106) may act as a manual switch, providing an additional means for the operator to control actuation of PETDD (100). In particular, when a vacuum is communicated to vacuum port (112), such a vacuum may be essentially ineffective until the operator manually covers or otherwise closes vent port (106). The vacuum may simply draw atmospheric air into an open vent port (106). Once the operator covers or otherwise closes vent port (106), the vacuum within housing (102) may provide the full apposition of the tympanic membrane (TM) against tip (122) and may provide the pressure differential that expands bellows (210) for actuation of trip mechanism (200). Regardless of whether a vent port (106) is provided, it should be understood that a hand switch, foot switch, and/or other type of user input may be interposed between a vacuum source and vacuum port (112) to provide the operator with further control of vacuum. It should also be understood that simply placing a finger over vent port (106) to close vent port (106) may impose less lateral force on PETDD (100) than pushing an activation button laterally on PETDD (100) might impose. Thus, vent port (106) may provide a greater stability and a reduced risk of inadvertent repositioning of PETDD (100) through operator error at the time of actuation.

Figure 12:
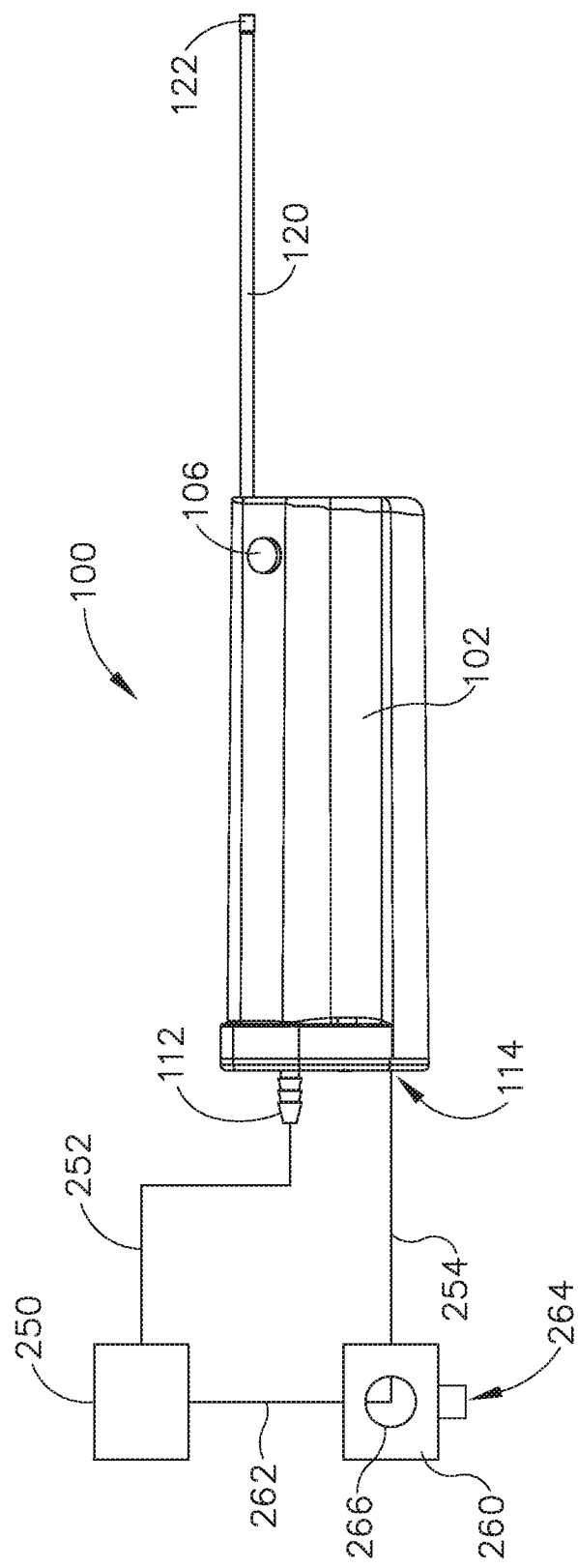
FIG. 12 depicts a side diagrammatic view of an exemplary alternative system incorporating the PETDD of FIG. 1.

FIG. 12 shows a merely exemplary alternative pneumatic configuration for PETDD (100). In this example, vacuum port (112) is directly coupled with a vacuum source (250) via a conduit (252). Vent port (114) is directly coupled with a valve assembly (260) via a conduit (254). Valve assembly (260) provides one fluid path leading to vacuum source (250) via a conduit (262); and another fluid path leading to a vent port (264). A valve (266) within valve assembly (260) selectively couples conduit (254) with either conduit (262) or vent port (264). In an exemplary use of this system, valve (266) may initially couple conduit (254) with conduit (262), such that the interior of housing (102) and the interior of bellows (210) receive the same vacuum simultaneously. In this example, bellows (210) remains compressed even when tip (122) achieves full apposition with the tympanic membrane (TM) since bellows (210) is not experiencing a pressure differential when valve (266) is positioned to couple conduit (254) with conduit (262). Once the operator is ready to actuate PETDD (100), the user may switch valve (266) to couple conduit (254) with port (114), thereby coupling the interior of bellows (210) with atmospheric air. Since the interior of housing (102) continues to receive a vacuum, this switching of valve (266) provides the pressure differential for expansion of bellows (210), which releases camshaft (130) for rotation as described above. Other suitable arrangements and pneumatic schemes will be apparent to those of ordinary skill in the art in view of the teachings herein.

II. Exemplary Pressure Equalization Tube

FIGS. 13-16 show PE tube (1200) in greater detail. PE tube (1200) of this example includes a cylindraceous body (1202) that defines a passageway (1204). A flange (1206) is located at the proximal end of body (1202) while a set of petals (1208) are located at the distal end of body (1202). Flange (1206) includes a plurality of inwardly directed recesses (1207). Recesses (1207) are configured to facilitate flexing of flange (1206) from an outwardly extended position to a generally cylindraceous position where the material forming flange (1206) extends longitudinally. While three recesses (1207) are shown, it should be understood that any other suitable number of recesses (1207) may be provided. Similarly, while three petals (1208) are shown, it should be understood that any other suitable number of petals (1208) may be provided.

PE tube (1200) is formed of a resilient material that is biased to assume the rivet like configuration shown in FIGS. 13-16. However, flange (1206) and petals (1208) may be flexed inwardly toward the longitudinal axis of body (1202) to provide PE tube (1200) with a cylindraceous configuration. In particular, flange (1206) and petals (1208) may be flexed such that their outer surfaces are at the same radial distance from the longitudinal axis as the outer perimeter of body (1202). This radial distance may be slightly less than the radial distance associated with the inner diameter of shield tube (160), such that PE tube (1200) may collapse to fit within shield tube (160). When PE tube (1200) is disposed in a tympanic membrane (TM), petals (1208) are located medially (i.e., on the middle ear side) while flange (1206) is located laterally (i.e., on the outer ear side). By way of example only, PE tube (1200) may also be configured in accordance with at least some of the teachings of U.S. patent application Ser. No. 13/800,113, entitled "Tympanic Membrane Pressure Equalization Tube," filed on Mar. 13, 2013, the disclosure of which is incorporated by reference herein; and/or at least some of the teachings of U.S. Pat. App. No. 13/804,553, entitled "Features to Improve and Sense Tympanic Membrane Apposition by Tympanostomy Tube Delivery Instrument," filed on March 14, 2013. the disclosure of which is incorporated by reference herein. Other suitable forms that PE tube (1200) may take will be apparent to those of ordinary skill in the art in view of the teachings herein.

III. Exemplary Dilator With Integral Cutting Features

In some instances, it may be desirable to consolidate the functionality of dilator tube (150) and piercer (180) in a single structure. In other words, it may be desirable to provide a component within cannula (120) that is operable to both create a myringotomy incision in the tympanic membrane (TM) like piercer (180) and expand the myringotomy incision like dilator tube (150). Such a component may be expandable in response to distal advancement of shield tube (160), similar to dilator tube (150). Such a component may also be driven by a cam follower like cam follower (152). The following examples represent merely illustrative variations of dilator tube (150) that are operable to both create a myringotomy incision in the tympanic membrane (TM) like piercer (180) and expand the myringotomy incision like dilator tube (150).

While the examples are provided herein in the context of PETDD (100), it should be understood that the variations of dilator tube (150) discussed below may also be readily incorporated into a variety of other PETDDs. By way of example only, the variations of dilator tube (150) discussed below may be readily incorporated in any of the PETDDs disclosed in U.S. Pub. No. 2010/0198135, the disclosure of which is incorporated by reference herein. As another merely illustrative example, the variations of dilator tube (150) discussed below may be readily incorporated into any of the PETDDs disclosed in U.S. Pat. App. No. 13/800,113, entitled "Tympanic Membrane Pressure Equalization Tube," filed on Mar. 13, 2013, the disclosure of which is incorporated by reference herein; and/or U.S. Pat. App. No. 13/804,553, the disclosure of which is incorporated by reference herein. Still other PETDD variations that may incorporate the variations of dilator tube (150) discussed below will be apparent to those of ordinary skill in the art in view of the teachings herein.

A. Exemplary Dilator with Sharp Distal Point

Figure 17:
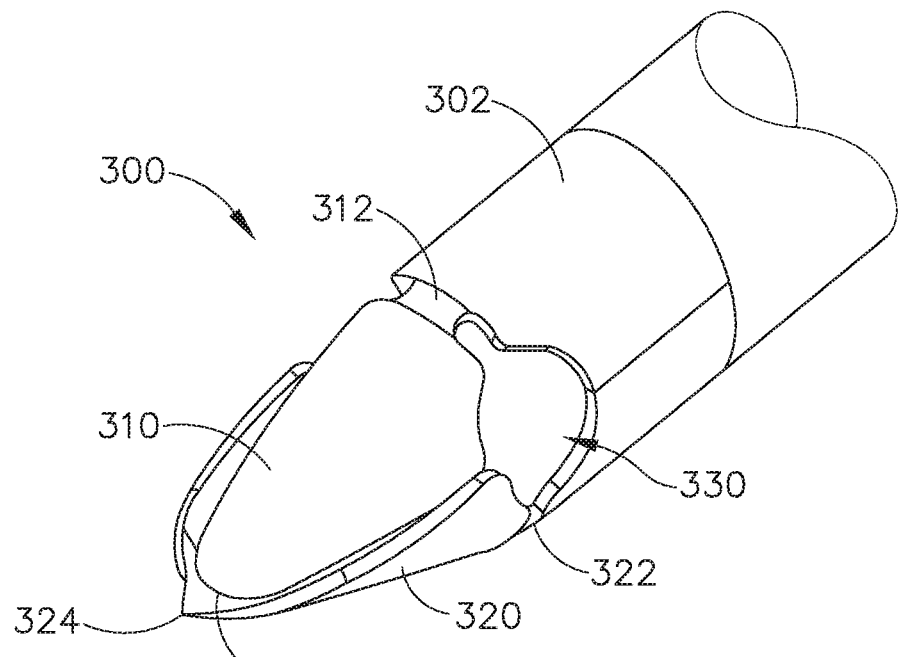
FIG. 17 depicts a perspective view of the distal end of an exemplary alternative dilator tube that may be readily incorporated in the PETDD of FIG. 1, in a collapsed state.
Figure 18:
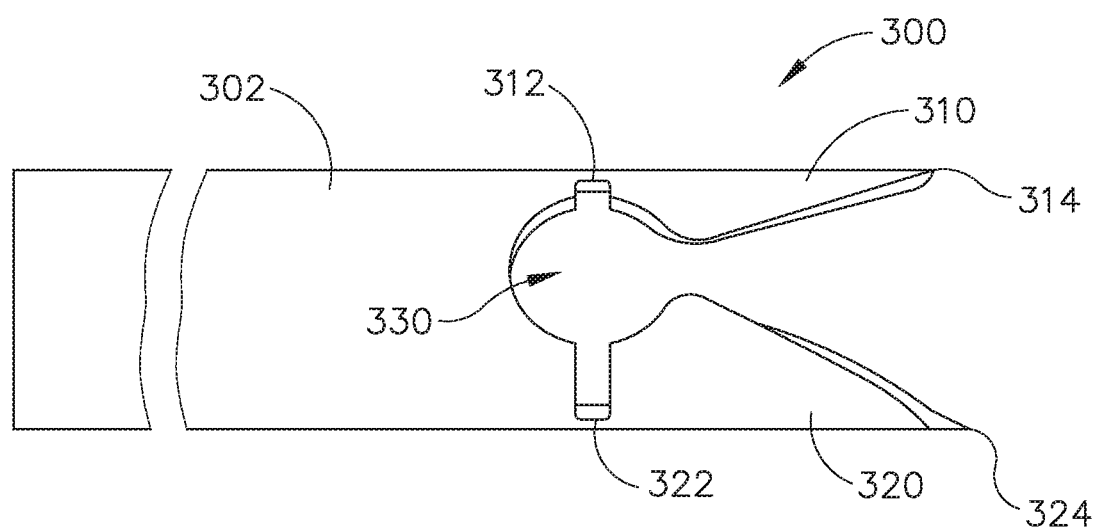
FIG. 18 depicts a side elevational view of the dilator tube of FIG. 17, in an expanded state.
Figure 19:
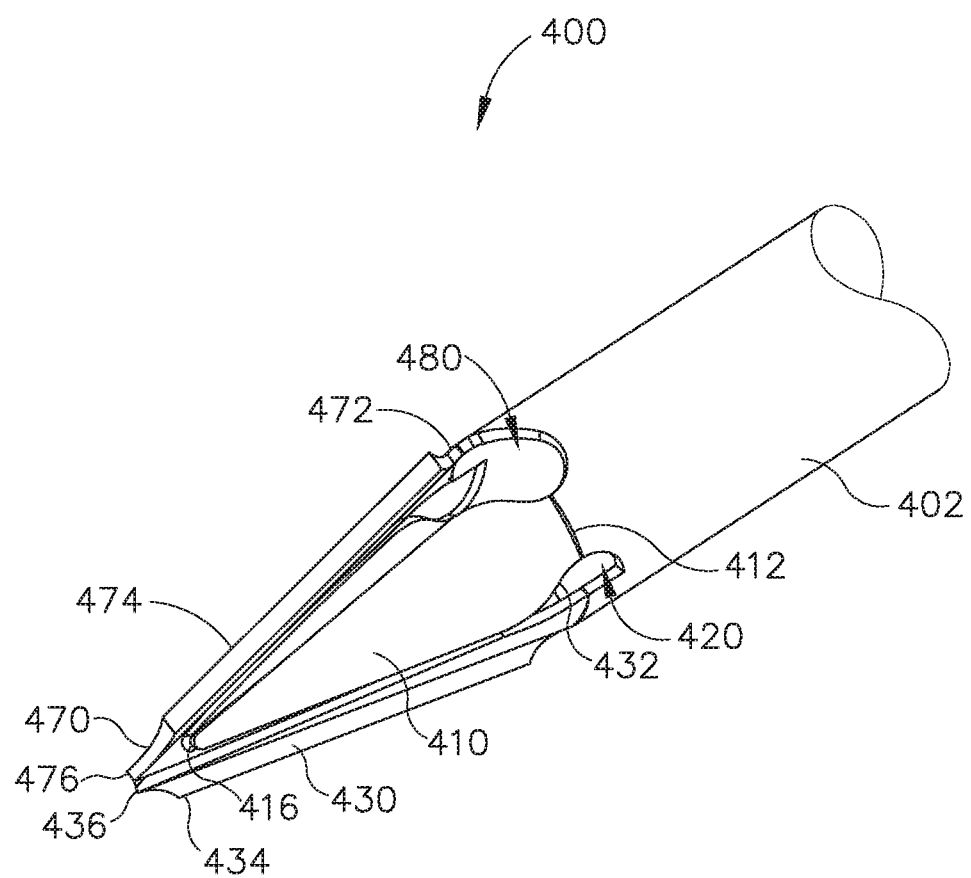
FIG. 19 depicts a perspective view of the distal end of another exemplary alternative dilator tube that may be readily incorporated in the PETDD of FIG. 1, in a collapsed state.
Figure 20:
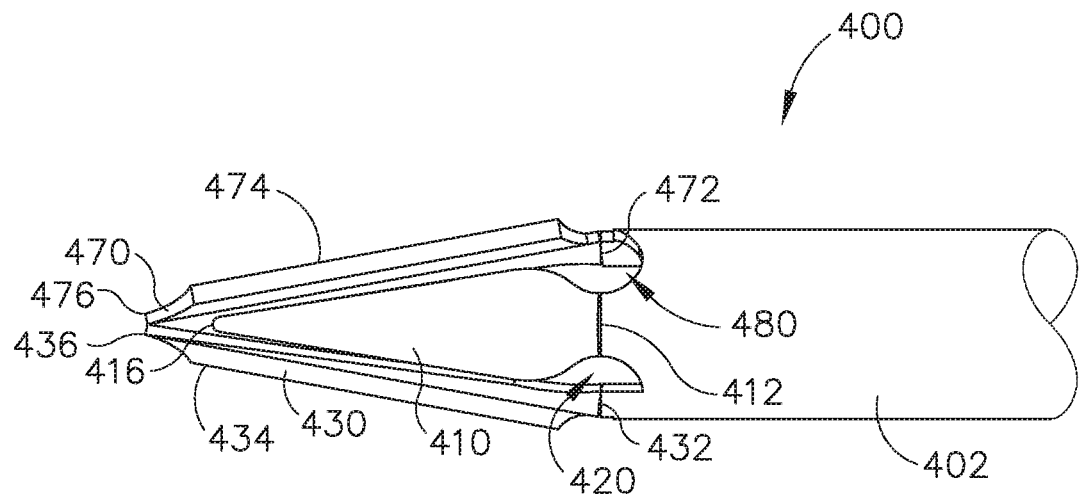
FIG. 20 depicts a side elevational view of the dilator tube of FIG. 19, in the collapsed state.
Figure 21:
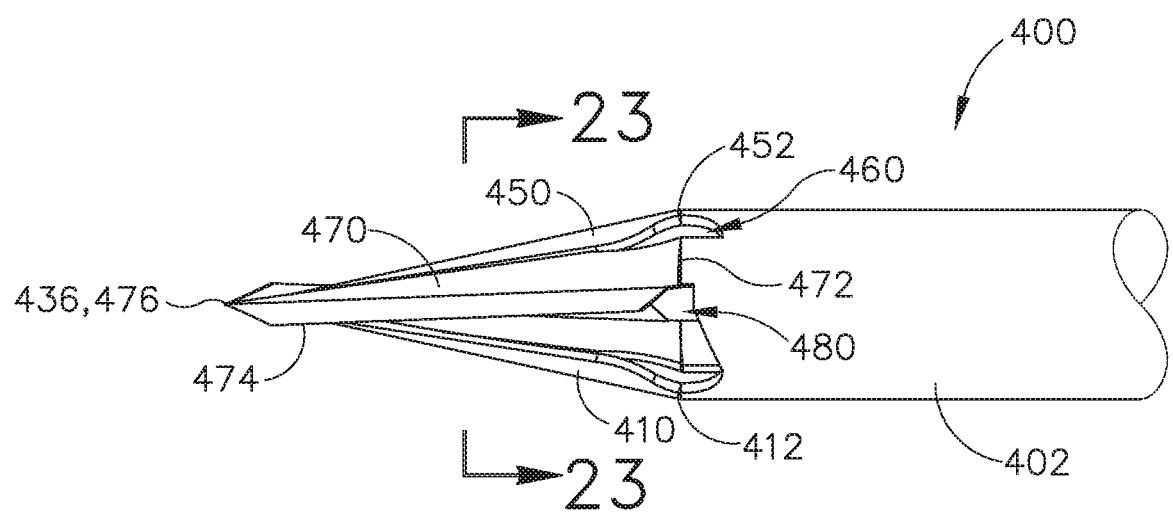
FIG. 21 depicts another side elevational view of the dilator tube of FIG. 19, in the collapsed state, rotated 90 degrees about the longitudinal axis of the dilator tube from the position shown in FIG. 20.
Figure 22:
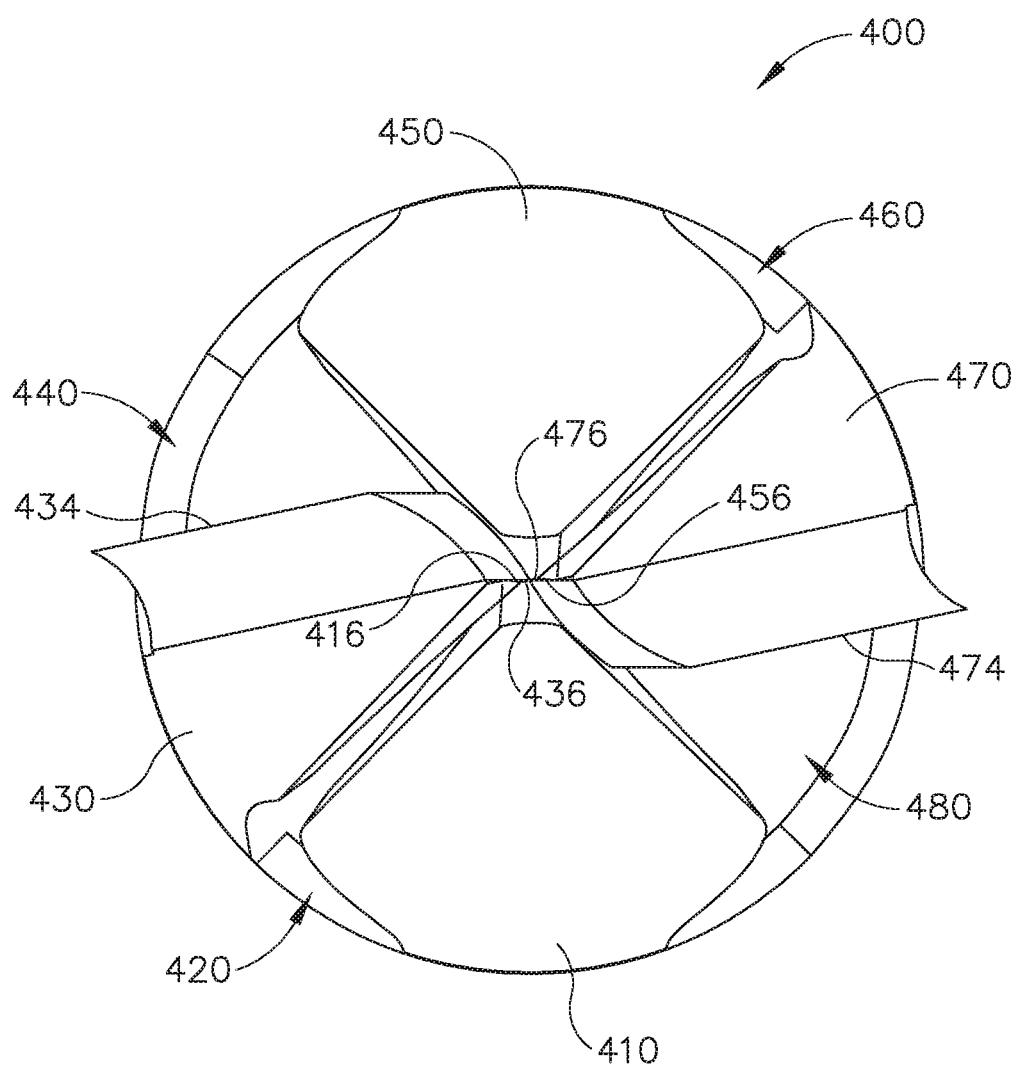
FIG. 22 depicts a distal end view of the dilator tube of FIG. 19, in the collapsed state.
Figure 23:
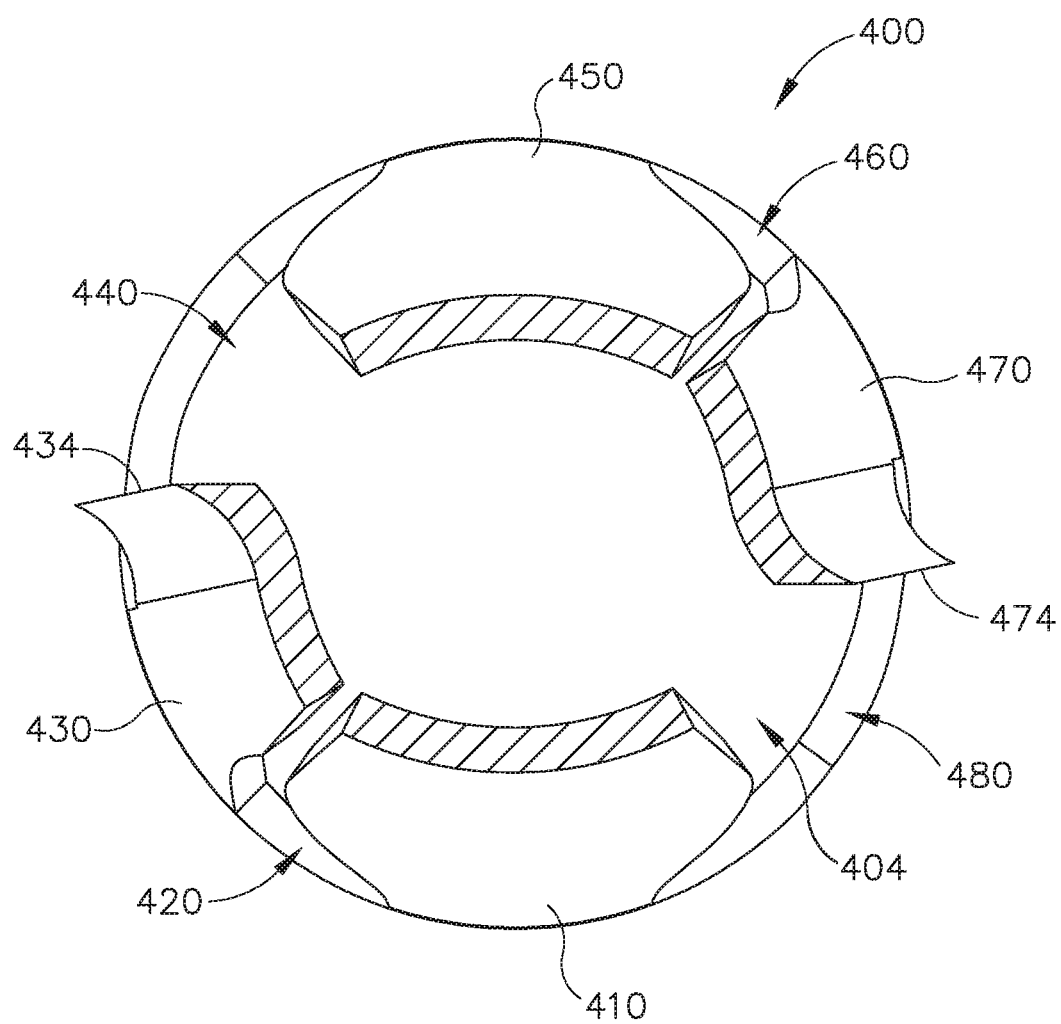
FIG. 23 depicts a cross-sectional view of the dilator tube of FIG. 19, taken along line 23-23 of FIG. 21.
Figure 24:
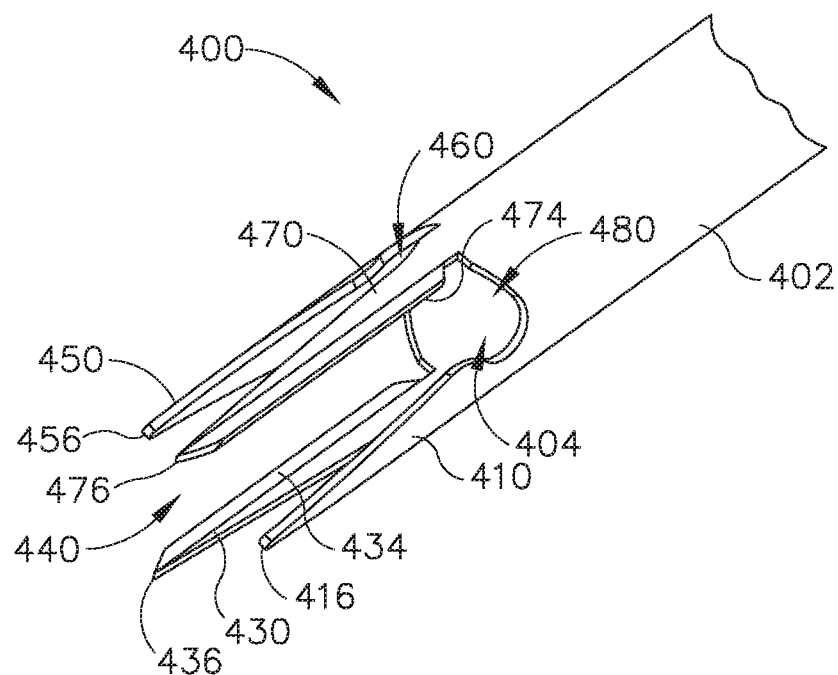
FIG. 24 depicts a perspective view of the dilator tube of FIG. 23, in an expanded state.
Figure 25:
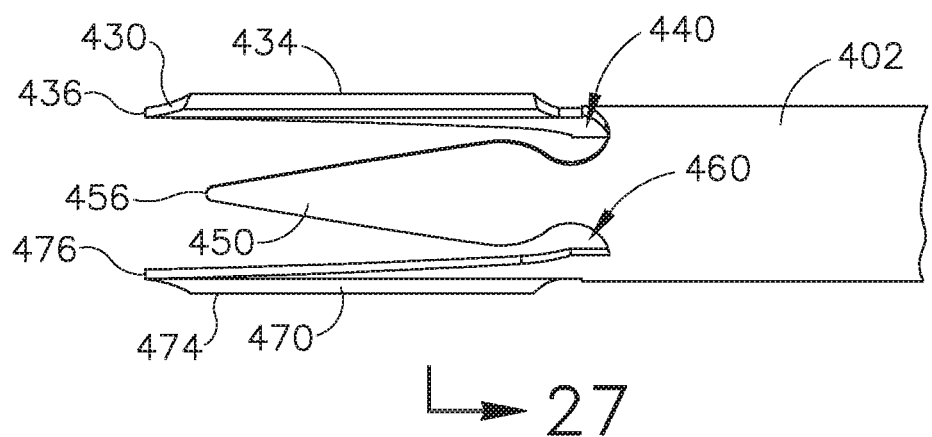
FIG. 25 depicts a side elevational view of the dilator tube of FIG. 19, in the expanded state.
Figure 26:
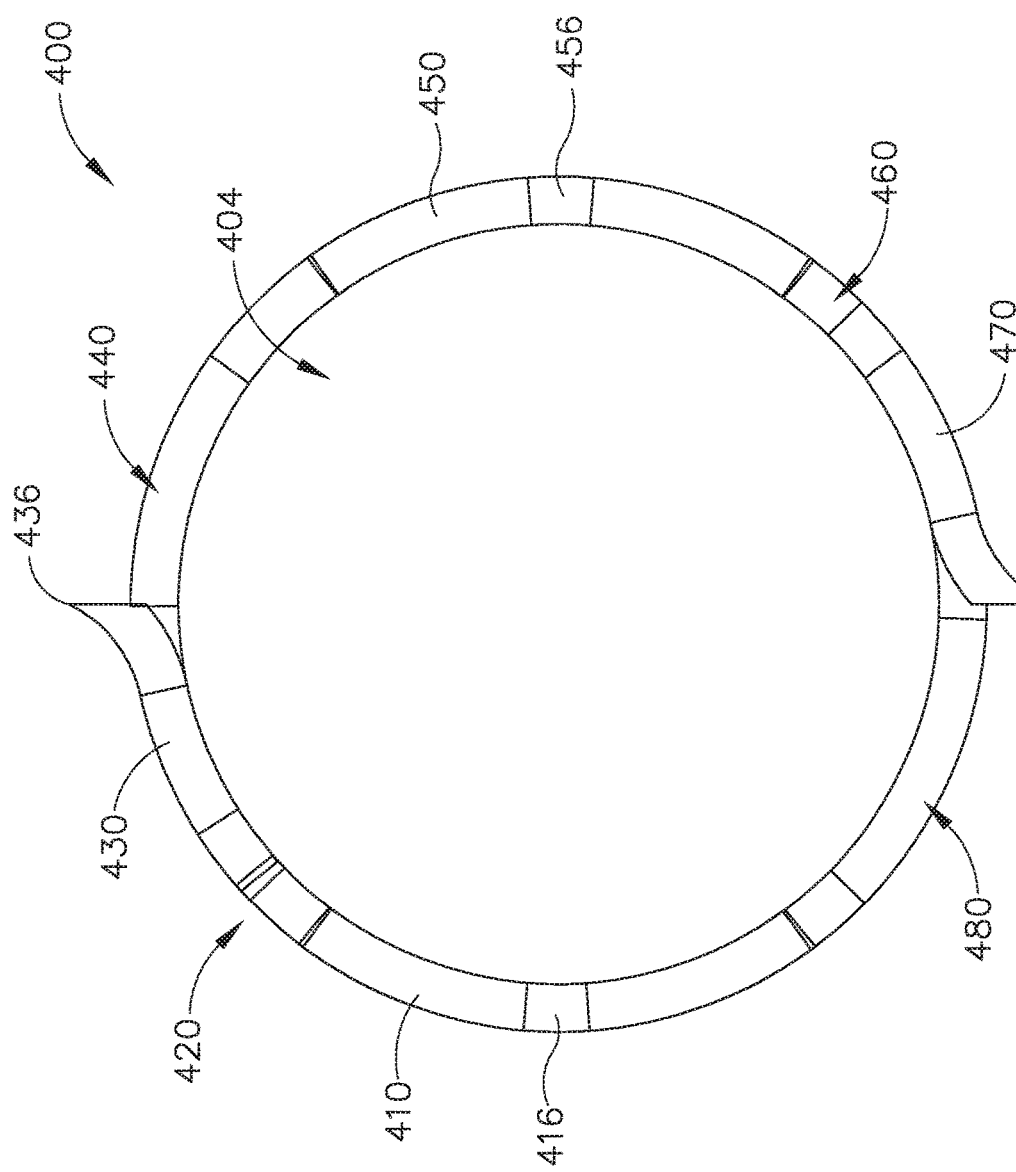
FIG. 26 depicts a distal end view of the dilator tube of FIG. 19, in the expanded state.

FIGS. 17-18 show an exemplary alternative dilator tube (300) that may be used in place of both dilator tube (150) and piercer (180) described above. In some versions, dilator tube (300) may be secured to cam follower (152) as a substitute for dilator tube (150). Furthermore, piercer (180) and cam follower (182) may simply be omitted from versions of a PETDD (100) that has dilator tube (300). Dilator tube (300) of the present example comprises a tubular portion (302) and two leaves (310, 320). Leaf (310) is joined to tubular portion (302) by a living hinge (312). Leaf (320) is also joined to tubular portion (302) by a living hinge (322). A pair of longitudinally extending gaps (330) are defined between leaves (310, 320). These gaps (330) include rounded regions near hinges (312, 322). As can be seen in FIG. 17, leaves (310, 320) present a duckbill configuration when dilator (300) is in a collapsed state.

Leaves (310, 320) are resiliently biased to assume the collapsed, inwardly deflected positioning shown in FIG. 17. However, leaves (310, 320) may flex at hinges (312, 322) and thereby deflect outwardly to the positions shown in FIG. 18, such that leaves (310, 320) align along the cylindraceous path defined by tubular portion (302). In particular, as shield tube (160) is advanced distally through the interior of tubular portion (302), the distal end of shield tube (160) drives leaves (312, 322) outwardly to the position shown in FIG. 18.

The distal edge (314) of leaf (310) is generally round. However, the distal edge of leaf (320) includes a sharp point (324). Sharp point (324) projects distally relative to distal edge (314), such that dilator tube (300) leads with sharp point (324). It should be understood that, as dilator tube (300) is driven into the tympanic membrane (TM), sharp point (324) will pierce the tympanic membrane (TM) and thereby create a myringotomy incision like piercer (180) would create. In some instances, the incision created by sharp point (324) is in the form of a substantially straight line. After sharp point (324) creates the incision, leaves (310, 320) may be held in place within the incision while shield tube (160) is advanced distally through the interior of tubular portion (302), eventually driving leaves (310, 320) outwardly within the incision to dilate the incision. Dilator tube (300) and shield tube (160) may then be retracted proximally while pusher tube (170) remains longitudinally stationary, resulting in deployment of PE tube (1200) in the tympanic membrane (TM) as described above.

It should be understood that eliminating piercer (180) in the present example provides a more open fluid path within the lumen of pusher tube (170). In other words, without piercer (180) being positioned in the lumen of pusher tube (170), pusher tube is now more effective at providing fluid communication to the distal end of cannula (120). By way of example only, this larger fluid path may more effectively communicate suction to the distal end of cannula (120) in versions where PETDD (100) is coupled with a vacuum source. As noted above, such suction may be used to assist in drawing the tympanic membrane (TM) against tip (122) to improve apposition between the tympanic membrane (TM) and tip (122). In addition or in the alternative, suction may be used to remove fluid from the middle ear, and the larger fluid path provided by the elimination of piercer (180) may facilitate communication of the fluid proximally through the lumen of pusher tube (170). This suction of fluid may be performed after PE tube (1200) is deployed in the tympanic membrane (TM), with the fluid being drawn through passageway (1204) of the deployed PE tube (1200) and tip (122). Thus, PETDD (100) may be used to suction fluid from the middle ear immediately after deployment of PE tube (1200), instead of having to use a separate suction instrument.

B. Exemplary Dilator with Sharp Longitudinal Edges

FIGS. 19-27 show another exemplary alternative dilator tube (400) that may be used in place of both dilator tube (150) and piercer (180) described above. In some versions, dilator tube (400) may be secured to cam follower (152) as a substitute for dilator tube (150). Furthermore, piercer (180) and cam follower (182) may simply be omitted from versions of a PETDD (100) that has dilator tube (400). Dilator tube (400) of the present example comprises a tubular portion (402) and four leaves (410, 430, 450, 470). Leaf (410) is joined to tubular portion (402) by a living hinge (412). Leaf (430) is joined to tubular portion (402) by a living hinge (432). Leaf (450) is joined to tubular portion (402) by a living hinge (452). Leaf (470) is joined to tubular portion (402) by a living hinge (472). Longitudinally extending gaps (420, 440, 460, 480) are defined between leaves (410, 430, 450, 470). These gaps (420, 440, 460, 480) include rounded regions near hinges (412, 432, 452, 472). As can be seen in FIGS. 19-22, the distal ends of leaves (410, 430, 450, 470) converge when dilator (400) is in a collapsed state.

Leaves (410, 430, 450, 470) are resiliently biased to assume the collapsed, inwardly deflected positioning shown in FIGS. 19-23. However, leaves (410, 430, 450, 470) may flex at hinges (412, 432, 452, 472) and thereby deflect outwardly to the positions shown in FIGS. 24-27, such that leaves (410, 430, 450, 470) align along the cylindraceous path defined by tubular portion (402). In particular, as shield tube (160) is advanced distally through the interior of tubular portion (402), the distal end of shield tube (160) drives leaves (410, 430, 450, 470) outwardly to the position shown in FIGS. 24-27.

Leaves (410, 450) are on diametrically opposed sides of tubular portion (402) and have pointed yet generally blunt distal tips (416, 456). Leaves (430, 470) are on diametrically opposed sides of tubular portion (402), offset by 90 degrees from leaves (410, 450), and have sharp edges (434, 474) extending along their respective lengths, with sharp distal tips (436, 476). As best seen in FIGS. 22-23 and 26-27, leaves (430, 470) are bent such that sharp edges (434, 474) project outwardly. In the present example, each sharp edge (434, 474) is formed at the convergence of a curved surface and a radially extending surface of the corresponding leaf (430, 470). When leaves (410, 430, 450, 470) are driven outwardly to an expanded state as shown in FIGS. 24-27, the full lengths of sharp edges (434, 474) are positioned outside the outer diameter of tubular portion (402). Sharp distal tips (436, 476) project distally relative to blunt distal tips (416, 456), such that dilator tube (400) leads with sharp distal tips (436 476).

By way of example only, sharp edges (434, 474) and sharp distal tips (436, 476) may be formed in a laser cutting process. For instance, initial forms of leaves (410, 430, 450, 470) may be laser cut from tubular portion (402). Then, an edge of each leaf (430, 470) may be bent outwardly. The outwardly bent edges may then be laser cut again (e.g., along the same path as a diameter of tubular portion (402)) to form sharp edges (434, 474) and sharp distal tips (436, 476). Other suitable ways in which various features of dilator tube (400) may be formed will be apparent to those of ordinary skill in the art in view of the teachings herein. While four leaves (410, 430, 450, 470) are provided in the present example, it should be understood that any other suitable number of leaves may be used. For instance, dilator tube (400) may include more than two sharpened leaves (430, 470), regardless of how many unsharpened leaves (410, 450) are provided.

It should be understood that, as dilator tube (400) is driven into the tympanic membrane (TM), sharp distal tips (436, 476) will pierce the tympanic membrane (TM) and thereby create a myringotomy incision like piercer (180) would create. After sharp distal tips (436, 476) create the incision, leaves (410, 430, 450, 470) may be held in place within the incision while shield tube (160) is advanced distally through the interior (404) of tubular portion (402), eventually driving leaves (410, 430, 450, 470) outwardly within the incision to dilate the incision. Sharp edges (434, 474) may perform additional cutting of the tympanic membrane (TM) during this dilation step, effectively increasing the length of the incision created by sharp distal tips (436, 476). Dilator tube (400) and shield tube (160) may then be retracted proximally while pusher tube (170) remains longitudinally stationary, resulting in deployment of PE tube (1200) in the tympanic membrane (TM) as described above.

As with dilator tube (300) described above, eliminating piercer (180) in the present example provides a more open fluid path within the lumen of pusher tube (170). In other words, without piercer (180) being positioned in the lumen of pusher tube (170), pusher tube is now more effective at providing fluid communication to the distal end of cannula (120). By way of example only, this larger fluid path may more effectively communicate suction to the distal end of cannula (120) in versions where PETDD (100) is coupled with a vacuum source. As noted above, such suction may be used to assist in drawing the tympanic membrane (TM) against tip (122) to improve apposition between the tympanic membrane (TM) and tip (122). In addition or in the alternative, suction may be used to remove fluid from the middle ear, and the larger fluid path provided by the elimination of piercer (180) may facilitate communication of the fluid proximally through the lumen of pusher tube (170). This suction of fluid may be performed after PE tube (1200) is deployed in the tympanic membrane (TM), with the fluid being drawn through passageway (1204) of the deployed PE tube (1200) and tip (122). Thus, PETDD (100) may be used to suction fluid from the middle ear immediately after deployment of PE tube (1200), instead of having to use a separate suction instrument.

IV. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method, comprising:
    positioning a shaft assembly proximate to a tympanic membrane of a patient, wherein the shaft assembly includes a first tubular member having a plurality of leaves disposed at a distal end of the first tubular member, the first tubular member having a cylindrical shape with an outer diameter, at least one of the plurality of leaves including a sharp distal tip configured to create an incision in the tympanic membrane and a distal edge configured to cut the tympanic membrane;
    advancing the first tubular member in a distal direction to create the incision in the tympanic membrane using the sharp distal tip of the at least one of the plurality of leaves;
    advancing a second tubular member disposed within a lumen of the first tubular member relative to the first tubular member in the distal direction to move the plurality of leaves from a collapsed position to an expanded position such that the distal edge of the at least one of the plurality of leaves cuts the tympanic membrane and increases a size of the incision, the distal edge of the at least one of the plurality of leaves being positioned outside of the outer diameter of the first tubular member when the plurality of leaves is in the expanded position.

2. The method of claim 1, further comprising:
    retracting the first and second tubular members relative to a third tubular member in a proximal direction, the third tubular member disposed within a lumen of the second tubular member and configured to deploy a tympanostomy tube; and
    deploying, in response to retracting the first and second tubular members, the tympanostomy tube in the incision using the third tubular member.

3. The method of claim 2, wherein the tympanostomy tube is disposed within the lumen of the second tubular member distal to the third tubular member;
    wherein deploying the tympanostomy tube includes pushing the tympanostomy tube out of the lumen of the second tubular member using the third tubular member.

4. The method of claim 2, further comprising:
    engaging a distal end of the third tubular member with a proximal end of the tympanostomy tube when the tympanostomy tube is deployed in the incision;
    applying a vacuum to the shaft assembly; and
    suctioning, in response to applying the vacuum, a fluid out from a middle ear of the patient through the tympanostomy tube and the third tubular member.

5. The method of claim 1, wherein the plurality of leaves includes four leaves,
    wherein each of two leaves of the four leaves includes a sharp distal tip configured to create an incision in the tympanic membrane and a distal edge configured to cut the tympanic membrane, the two leaves disposed on diametrically opposed sides of the distal end of the first tubular member.

6. The method of claim 1, wherein the at least one of the plurality of leaves includes a curved surface and a radially extending surface, and wherein the distal edge is defined at a convergence of the curved surface and the radially extending surface.

7. The method of claim 1, wherein the distal edge of the at least one of the plurality of leaves projects in a direction parallel to a longitudinal axis of the first tubular member when the plurality of leaves is in the expanded position.

8. The method of claim 1, further comprising:
    applying a vacuum to an interior of the shaft assembly;
    engaging a distal end of the shaft assembly with the tympanic membrane such that the vacuum generates a change in pressure in the interior of the shaft assembly;
    expanding, in response to the change in pressure, a bellows from a first state in which a pivoting member engages a camshaft to a second state in which the pivoting member releases the camshaft; and
    rotating, in response to the pivoting member releasing the camshaft, the camshaft,
    wherein the first tubular member is advanced in the distal direction in response to rotating the camshaft.

9. The method of claim 8, wherein the bellows is collapsed in the first state and expanded in the second state.

10. The method of claim 8, wherein expanding the bellows from the first state to the second state includes connecting an interior of the bellows to atmospheric air exterior to the shaft assembly.

11. An apparatus, comprising:
    a body; and
    a shaft assembly extending distally from the body, the shaft assembly including:
        a tubular member disposed within the shaft assembly and having a cylindrical shape with an outer circumference; and
        a plurality of leaves disposed at a distal end of the tubular member, wherein the plurality of leaves is movable between a collapsed position and an expanded position, the plurality of leaves including a first leaf including a sharp distal point configured to create an incision in a tympanic membrane of a patient and a second leaf including a blunt distal point, the first leaf extending around a greater portion of the outer circumference than the second leaf,
        wherein the plurality of leaves define a plurality of longitudinally-extending gaps, each of the plurality of longitudinally-extending gaps disposed between two leaves of the plurality of leaves.

12. The apparatus of claim 11, wherein the connection between the tubular member and the plurality of leaves includes a living hinge.

13. The apparatus of claim 11, wherein the sharp distal point is configured to create a straight-line incision when the plurality of leaves move between the collapsed position and the expanded position.

14. The apparatus of claim 11,
wherein the first leaf has a longitudinal length greater than a longitudinal length of the second leaf.

15. An apparatus, comprising:
a shaft assembly having a distal end, the shaft assembly including:
  a tubular member disposed within the shaft assembly; and
  a plurality of leaves disposed at a distal end of the tubular member, wherein at least one of the plurality of leaves includes a sharp distal point configured to create an incision in a tympanic membrane of a patient;
a vacuum source in fluid communication with the shaft assembly and configured to provide suction at the distal end of the shaft assembly;
a drive mechanism configured to drive movement of the tubular portion and the plurality of leaves to create the incision in the tympanic membrane; and
a trigger mechanism configured to activate the drive mechanism, the trigger mechanism including:
  a pivoting member having an end configured to move between a first position in which the second end is engaged with the drive mechanism and a second position in which the second end releases the drive mechanism; and
  a bellows configured to expand from a collapsed state to an expanded state when the interior of the bellows is in fluid communication with atmospheric air to move the pivoting member from the first position to the second position to activate the drive mechanism,
  wherein the bellows moves the pivoting member from the first position to the second position when the distal end of the shaft assembly engages with the tympanic membrane.

16. The apparatus of claim 15, further comprising a valve assembly including a vent port in fluid communication with atmospheric air,
  wherein the valve assembly is in fluid communication with the vacuum and the interior of the bellows, and
  wherein the valve assembly is configured to selectively couple the interior of the bellows to one of the vacuum and the vent port,
  wherein the bellows is configured to move the pivoting member from the first position to the second position when the interior of the bellows is coupled to the vent port via the valve assembly.

17. The apparatus of claim 16, wherein the bellows expands from the collapsed state to the expanded state when the distal end of the shaft assembly engages with the tympanic membrane and the interior of the bellows is coupled to the vent port.

18. The apparatus of claim 15, wherein the vacuum source generates a negative pressure when the distal end of the shaft assembly engages with the tympanic membrane, and wherein the bellows expands from the collapsed state to the expanded state in response to the negative pressure.

* * * * *